United States Patent [19]

Sakai et al.

[11] 4,012,429
[45] Mar. 15, 1977

[54] 16,16-DIMETHYL 9-OXO-11α-HYDROXYMETHYL-15ε-HYDROXYPROSTA-5(CIS), 13(TRANS)-DIENOIC ACID DERIVATIVES AND PROCESS FOR THE PREPARATION THEREOF

[75] Inventors: Kiyoshi Sakai; Osamu Oda; Takashi Yusa; Mitsuo Yamazaki; Masaaki Sasaki; Kazuhiko Sasagawa, all of Tokyo, Japan

[73] Assignee: Sankyo Company Limited, Tokyo, Japan

[22] Filed: Apr. 3, 1974

[21] Appl. No.: 457,564

[30] Foreign Application Priority Data

Apr. 19, 1973  Japan .................... 48-44444

[52] U.S. Cl. .............. 260/468 D; 260/240 R; 260/345.8; 260/413; 260/514 D; 260/343.3 R; 260/410.9 R; 260/463; 424/305; 424/317
[51] Int. Cl.² ......................... C07C 177/00
[58] Field of Search .............. 260/468 D, 514 D

[56] References Cited

UNITED STATES PATENTS

| | | | |
|---|---|---|---|
| 3,816,393 | 6/1974 | Hayashi et al. | 260/204 |
| 3,845,042 | 10/1974 | Strike et al. | 260/240 |
| 3,849,474 | 11/1974 | Abraham et al. | 260/468 |
| 3,931,282 | 1/1976 | Muchowski et al. | 260/468 |

FOREIGN PATENTS OR APPLICATIONS

| | | | |
|---|---|---|---|
| 2,313,868 | 10/1973 | Germany | 260/468 |
| 7,311,403 | 2/1974 | Netherlands | 260/468 |

OTHER PUBLICATIONS

Robert, Research in Prostaglandins, Worcester Foundation for Experimental Biology, Jan. 1973.
Corey et al., JACS, 92, 397, (1970).

*Primary Examiner*—Robert Gerstl
*Attorney, Agent, or Firm*—Flynn & Frishauf

[57] ABSTRACT

Prostanoic acid derivatives having the formula

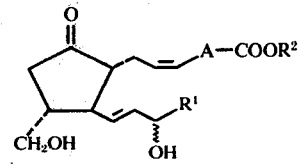

wherein A represents a straight or branched alkylene group having from one to 5 carbon atoms, $R^1$ represents a straight or branched alkyl group having from 4 to 10 carbon atoms and $R^2$ represents hydrogen atom or a straight or branched alkyl group having from one to 6 carbon atoms and pharmaceutically acceptable salts thereof.

The compounds are useful as oxytocic agents and agents inhibiting the secretion of gastric acid and may be prepared by oxidizing a compound having the formula

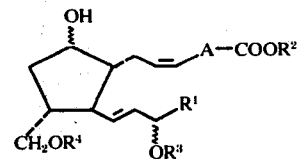

wherein A, $R^1$ and $R^2$ are the same as above, $R^3$ and $R^4$ are the same or different and each represents a protecting group for the hydroxyl group to give a compound having the formula

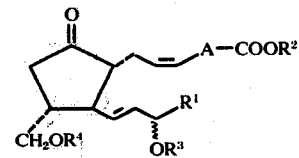

wherein A, $R^1$, $R^2$, $R^3$ and $R^4$ are the same as above, removing the hydroxyl-protecting group from the latter compound and, if appropriate, salifying the product thus obtained.

4 Claims, No Drawings

16,16-DIMETHYL 9-OXO-11α-HYDROXYMETHYL-15ε-HYDROXY-PROSTA-5(CIS), 13(TRANS)-DIENOIC ACID DERIVATIVES AND PROCESS FOR THE PREPARATION THEREOF

This invention relates to novel prostanoic acid derivatives and a novel process for the preparation thereof.

More particularly, it relates to 9-oxo-11α-hydroxymethyl-15ε-hydroxyprosta-5(cis), 13(trans)-dienoic acid derivatives having the formula

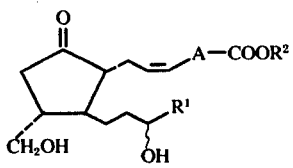

wherein A represents a straight or branched alkylene group having from one to 5 carbon atoms, $R^1$ represents a straight or branched alkyl group having from 4 to 10 carbon atoms and $R^2$ represents hydrogen atom or a straight or branched alkyl group having from one to 6 carbon atoms and pharmaceutically acceptable salts thereof and also relates to a process for the preparation thereof.

In the above formula (I), A may be a straight or branched alkylene group having from one to 5 carbon atoms, preferably, methylene, ethylene, trimethylene, propylene, tetramethylene, 1,2-butylene, 1,3-butylene, pentamethylene, 1,2-amylene, 2,3-amylene and 1,4-amylene, $R^1$ may be a straight or branched alkyl group having from 4 to 10 carbon atoms, preferably, n-butyl, isobutyl, n-pentyl, isopentyl, 1-methylpentyl, 2-methylpentyl, 1,1-dimethylpentyl, 1,2-dimethylpentyl, n-hexyl, isohexyl, 1-methylhexyl, 1,1-dimethylhexyl, 1,2-dimethylhexyl, n-heptyl, n-octyl and n-decyl. $R^2$ may be hydrogen atom or a straight or branched alkyl group having from one to 6 carbon atoms, preferably, methyl, ethyl, n-propyl, isopropyl, n-butyl, isobutyl, n-pentyl and n-hexyl. Preferred groups of the prostanoic acid derivatives provided by the invention are those of the formula (I) wherein A represents trimethylene group, i.e., those having the formula

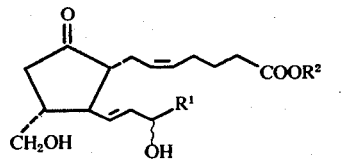

wherein $R^1$ and $R^2$ are the same as above and the pharmaceutically acceptable salts thereof.

In formulae (I) and (I-a), and elsewhere in this specification, a bond attached to the cyclopentane nucleus which is in the α-configuration, i.e., extends below the plane of the cyclopentane ring, is represented by a dotted line, and a bond which is in the β-configuration, i.e., extends above the plane of the cyclopentane ring, is represented by a solid line. The wavy line indicates that either steric configuration is possible. In the scope of this invention, optical isomers and racemic mixtures of the prostanoic acid derivatives having the formula (I) may be contained.

The pharmaceutically acceptable salts of the acids of formulae (I) and (I-a) in which $R^2$ is hydrogen atom include alkali and alkaline earth metal salts, e.g., the sodium, potassium, magnesium and calcium salts, quaternary ammonium salts, e.g., the ammonium, tetramethylammonium, tetraethylammonium, benzyltrimethylammonium and phenyltriethylammonium salts, aliphatic, alicyclic or aromatic amine salts, e.g., the methylamine, ethylamine, dimethylamine, diethylamine, trimethylamine, triethylamine, N-methylhexylamine, cyclopentylamine, dicyclohexylamine, benzylamine, dibenzylamine, α-phenylethylamine and ethylenediamine salts, heterocyclic amine salts, e.g., the piperidine, morpholine, pyrrolidine, piperazine, pyridine, 1-methylpiperazine and 4-ethylmorpholine salts, salts of amines which are water-soluble or contain a hydrophilic group, e.g., the monoethanolamine, ethyldiethanolamine and 2-amino-1-butanol salts. Such salts may be prepared from the acids of formulae (I) and (I-a) in which $R^2$ is hydrogen atom by the conventional techniques.

The followings are examples of compounds according to the invention;

9-oxo-11α-hydroxymethyl-15α(or β)-hydroxyprosta-5(cis), 13(trans)-dienoic acid;

methyl 9-oxo-11α-hydroxymethyl-15α(or β)-hydroxyprosta-5(cis),13(trans)-dienoate;

potassium 9-oxo-11α-hydroxymethyl-15α(or β)-hydroxyprosta-5(cis),13(trans)-dienoate;

9-oxo-11α-hydroxymethyl-15α(or β)-hydroxy-16,16-dimethylprosta-5(cis),13(trans)-dienoic acid;

methyl 9-oxo-11α-hydroxymethyl-15α(or β)-hydroxy-16,16-dimethylprosta-5(cis),13(trans)-dienoate;

potassium 9-oxo-11α-hydroxymethyl-15α(or β)-hydroxy-16,16-dimethylprosta-5(cis),13(trans)-dienoate;

9-oxo-11α-hydroxymethyl-15α(or β)-hydroxy-20-ethylprosta-5(cis),13(trans)-dienoic acid;

methyl 9-oxo-11α-hydroxymethyl-15α(or β)-hydroxy-20-ethylprosta-5(cis),13(trans)-dienoate;

potassium 9-oxo-11α-hydroxymethyl-15α(or β)-hydroxy-20-ethylprosta-5(cis),13(trans)-dienoate;

9-oxo-11α-hydroxymethyl-15α(or β)-hydroxy-20-methylprosta-5(cis),13(trans)-dienoic acid;

9-oxo-11α-hydroxymethyl-15α(or β)-hydroxy-16,16-dimethyl-20-methylprosta-5(cis),13(trans)-dienoic acid;

9-oxo-11α-hydroxymethyl-15α(or β)-hydroxy-16,16-dimethyl-20-ethylprosta-5(cis),13(trans)-dienoic acid;

9-oxo-11α-hydroxymethyl-15α(or β)-hydroxy-20-propylprosta-5(cis),13(trans)-dienoic acid.

The compounds of the invention exhibit oxytocic activities and are useful as oxytocic agents. The compounds of this invention were dissolved in an isotonic sodium chloride solution containing a small amount of sodium bicarbonate and administered to full-term pregnant rats by intravenous injection. The oxytocic activities of the compounds were measured by recording the changes in the intra-amniotic pressure [the method described by M. Hogaki, et al., Acta Obsterica Gynaecologica Japonica 19, 118–124 (1972)]. The results are shown in Table 1.

Furthermore, the compounds of this invention exhibit secretion activities of gastric acid and are useful as agents inhibiting the secretion of gastric acid.

The compounds of this invention were administered to rats by intravenous injection and their secretion activities of gastric acid were tested by Ghosh & Shild test method described in Brit. J. Pharmacol. 13, 354 (1958). The amounts of the compounds to raise the pH of intragastric perfusate by one are shown in Table 1.

Table 1

| Test compound | Oxytocic activities in rat ($\mu$g/kg) | Secretion activities of gastric acid in rat ($\mu$g/kg/hr) |
|---|---|---|
| 9-Oxo-11$\alpha$-hydroxymethyl-15$\alpha$-hydroxy-prosta-5(cis),13(trans)-dienoic acid | 35 | 2.4 |
| 9-Oxo-11$\alpha$-hydroxymethyl-15$\alpha$-hydroxy-16,26-dimethylprosta-5(cis),13(trans)-dienoic acid | 1.25 | 0.037 |
| 9-Oxo-11$\alpha$-hydroxymethyl-15$\alpha$-hydroxy-20-ethylprosta-5(cis),13(trans)-dienoic acid | 250 | 1.8 |
| Prostaglandin $E_2$. | 5 | 0.13 |
| Prostaglandin $F_2\alpha$ | 35 | — |

Accordingly, the compounds of this invention are useful medically as oxytocic agents and agents inhibiting the secretion of gastric acid; and the invention provides pharmaceutical compositions comprising a compound of formula (I), or a pharmaceutically acceptable salt thereof, and a pharmaceutical carrier or diluent. The pharmaceutical compositions of this invention are generally formulated for oral or parenteral administration. In case of employing the compounds (I) as oxytocic agents, the compounds (I) may be preferably administered by continuous intravenous infusion, dissolved in sterile pyrogen-free isotonic sodium chloride solution. The optimum dosage of the compounds (I) will vary with the body weight and age of the patient, but the parenteral total daily dosage for full-term pregnant women will generally be from 0.1 mg. to 100 mg.

In case of employing the compounds (I) as agents inhibiting the secretion of gastric acid, the compounds (I) may be preferably administered orally or by intravenous infusion and the oral or parenteral total daily dosage for adults will generally be from 0.01 mg. to 100 mg. Compositions suitable for oral use may be, for example, in the form of tablets, capsules, solutions or suspensions in aqueous media or in non-toxic organic liquid media, or dispersible powders suitable for the preparation of liquid suspensions.

In accordance with the process of the present invention, a compound having the aforementioned general formula (I) may be obtained by oxidizing a compound having the formula

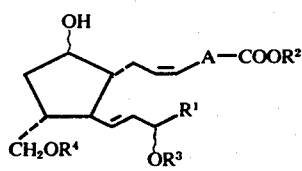

(II)

wherein A, $R^1$ and $R^2$ are the same as above, $R^3$ and $R^4$ are same or different and each represents a protecting group for the hydroxyl group to give a compound having the formula

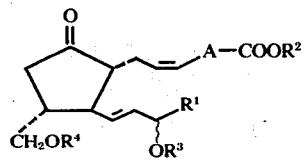

(III)

wherein A, $R^1$, $R^2$, $R^3$ and $R^4$ are the same as above, removing the hydroxyl-protecting group from the latter compound and, if appropriate, salifying the product thus obtained. The protective groups, $R^3$ and $R^4$, may be any of those which do not affect other parts of the compound in the subsequent reaction for removing the employed protecting group and replacing by a hydrogen atom, and may be exemplified by a heterocyclic group such as 2-tetrahydropyranyl, 2-tetrahydrothiopyranyl, 2-tetrahydrothienyl or 4-methoxytetrahydropyran-4-yl, an alkoxyhydrocarbon group such as methoxymethyl, ethoxymethyl, 1-ethoxyethyl or 1-methoxycyclohexane-1-yl, a hydrocarbon group such as methyl, ethyl, n-propyl or isopropyl, a trialkyl silyl group such as trimethylsilyl or triethylsilyl, a carbonic acid residue of ester such as benzyloxycarbonyl, phenethyloxycarbonyl, methoxycarbonyl or ethoxycarbonyl and an acyl group which may be substituted with a halogen atom such as acetyl, trichloroacetyl, trifluoroacetyl, propionyl, benzoyl or p-phenylbenzoyl, but it is not limited to these protecting groups.

In carrying out the process of the present invention, the reaction for oxidizing the compound having the aforementioned general formula (II) to produce the compound having the aforementioned general formula (III) is conducted by the use of an oxidizing agent in the presence or absence of a solvent. The oxidizing agents to be employed may preferably be chromic acids such as chromic acid, chromic anhydride, a chromic anhydride - pyridine complex (Collins reagent), chromic anhydride - conc. sulfuric acid - water (Jones reagent), sodium biochromate and potassium bichromate, organic active halogen compounds such as N-bromoacetamide, N-bromosuccinimide, N-bromophthalimide, N-chloro-p-toluenesulfonamide and N-chlorobenzenesulfonamide; aluminum alkoxides such as aluminum tert-butoxide and aluminum isopropoxide, dimethylsulfoxide - dicyclohexylcarbodiimide, dimethylsulfoxide - acetic anhydride and the like.

The solvents to be employed in the case of using a solvent are not limited so far as these are inert to the present reaction and are preferably organic solvents or mixture solutions of organic acids and organic acid anhydrides such as, acetic acid and acetic acid - acetic anhydride or halogenated hydrocarbons such as dichloromethane, chloroform and carbon tetrachloride in cases where chromic acids are employed. While, in cases where organic active halogen compounds are employed, aqueous organic solvents such as aqueous tert-butanol, aqueous acetone and aqueous pyridine are preferred. In cases where aluminum alkoxides are employed, aromatic hydrocarbons such as benzene, toluene and xylene are preferred. In cases where either dimethylsulfoxide - dicyclohexylcarbodiimide or dimethylsulfoxide - acetic anhydride is employed and an excess amount of the dimethylsulfoxide is used, no other solvents are generally needed. In cases where aluminum alkoxides are employed, excess amounts of hydrogen acceptors, for instance, ketones such as acetone, methyl ethyl ketone, cyclohexanone and benzoquinone are preferably used as well as the above-mentioned solvent. In carrying out this reaction, water should be completely expelled from the reaction system. In cases where dimethylsulfoxide - dicyclohexylcarbodiimide is employed, such acids as phosphoric acid, acetic acid and the like are used in the catalytic amount in accordance with a conventional manner. In the present reaction, chromic acids, especially a chromic anhydride - pyridine complex (Collins reagent) and chromic anhydride - conc. sulfuric acid - water (Jones reagent), are employed as most preferred oxidizing agents.

The reaction temperature is not limited, but it is preferable to be relatively lower so as to avoid side reactions. The reaction may be usually performed at a temperature from $-20°$ C to room temperature and preferably at a temperature from $0°$ C to room temperature. The reaction time may vary mainly depending upon the reaction temperature and the kind of oxidizing agents used and may be between about 10 minutes and 1 hour.

After completion of the reaction, the desired compound of the oxidizing reaction is taken out of the reaction mixture in a usual way. For example, it is obtained by adding an organic solvent such as ether to the reaction mixture after the reaction is completed, removing the insoluble materials, washing and drying the resulting organic layer and evaporating the solvent from the organic layer. The desired compound thus obtained may be further purified in a usual way, for example, column chromatography or thin layer chromatography, if needed.

The reactions for removing the protecting groups for the hydroxyl group are different depending upon the kinds of the protecting groups. For example, in cases where the protecting group for the hydroxyl group is the heterocyclic group or the alkoxyhydrocarbon group, the reaction may be easily achieved by bringing the compound into contact with an acid. The acids to be employed may preferably be, for example, organic acids such as formic acid, acetic acid, propionic acid, butyric acid, oxalic acid and malonic acid or mineral acids such as hydrochloric acid, hydrobromic acid and sulfuric acid. The reaction may be carried out in the presence or absence of a solvent. Yet, the use of a solvent is preferred in order to carry out the reaction smoothly. The solvents to be employed are not limited so far as these are inert to the present reaction, and preferably are water, alcohols such as methanol and ethanol, ethers such as tetrahydrofuran and dioxane, and mixed solvents of the said organic solvents with water. The reaction temperature is not specifically limited and may be between room temperature and the reflux temperature of the solvent to be used.

In cases where the protecting group for the hydroxyl group is, for instance, a hydrocarbon group, the reaction may be easily achieved by bringing the compound into contact with boron halide such as boron trichloride or boron tribromide. The reaction may be carried out in the presence of absence of a solvent. Yet, the use of a solvent is preferred in order to carry out the reaction smoothly. The solvents to be employed are not limited so far as these are inert to the present reaction, and preferably are, for instance, halogenated hydrocarbons such as dichloromethane and chloroform. The reaction temperature is not specifically limited, but relatively lower temperatures may be desired so as to avoid side reactions. Temperatures between $-30°$ C and room temperature may be preferred.

In cases where the protecting group for the hydroxyl group is, for instance, the trialkylsilyl group, the reaction may be easily achieved by bringing the compound into contact with water or water containing an acid or base. The acid or a base to be employed where the water containing an acid or a base is used may be unlimited, for instance, an acid such as an organic acid such as formic acid, acetic acid, propionic acid, butyric acid, oxalic acid or malonic acid or a mineral acid such as hydrochloric acid, hydrobromic acid or sulfuric acid or a base such as a hydroxide of an alkali metal or an alkaline earth metal such as potassium hydroxide or calcium hydroxide or a carbonic acid salt of an alkali metal or an alkaline earth metal such as potassium carbonate or calcium carbonate. In carrying out this reaction by the use of water, other solvents are not specifically needed. In cases where other solvents are employed, mixed solvents of water with organic solvents, for instance, ethers such as tetrahydrofuran and dioxane and alcohols such as methanol and ethanol are used. The reaction temperature is not specifically limited, but room temperature may be conveniently employed in general.

In cases where the protecting group for the hydroxyl group is, for instance, the carbonic acid residue of ester, or the acyl group, the reaction may be easily achieved by bringing the compound into contact with an acid or a base. The acids or the bases to be employed may preferably be, for instance, mineral acids such as hydrochloric acid, hydrobromic acid and sulfuric acid, hydroxides of alkali metals and alkaline earth metals such as sodium hydroxide, potassium hydroxide and calcium hydroxide and carbonic acid salts of alkali metals and alkaline earth metals such as sodium carbonate, potassium carbonate and calcium carbonate. The reaction may generally and conveniently be carried out under basic conditions. The reaction may be conducted in the presence or absence of a solvent. Yet, the use of a solvent is preferred in order to carry out the reaction smoothly. The solvents to be employed are not limited so far as these are inert to the present reaction, and preferably are, for instance, water, alcohols such as methanol and ethanol, ethers such as tetrahydrofuran and dioxane or mixed solvents of water with these organic solvents. The reaction temperature is not specifically limited, but temperatures between room temperature and the reflux temperature of the solvent used are preferred. It varies depending mainly upon the kind of the protecting groups to be removed.

After completion of the reaction, the desired compound of the reaction for removing the protecting group for the hydroxyl group may be taken out of the reaction mixture according to a usual way. For example, it is obtained by neutralizing the reaction mixture, extracting it after addition of an adequate organic solvent and evaporating the solvent from the resulting extract. The desired compound thus obtained may, if needed, be further purified by a conventional method, for example, column chromatography and thin layer chromatography.

The compounds having the formula (I) wherein $R_2$ is hydrogen atom may be alternatively obtained by hydrolyzing the compound having the formula (I) wherein $R_2$ is the alkyl group. The reaction may be achieved by bringing the compound having the formula (I) wherein $R_2$ is the alkyl group into contact with an acid or base. The acid or base to be employed is any one which may be used in a conventional hydrolysis, and may preferably be, for instance, a mineral acid such as hydrochloric acid, hydrobromic acid or sulfuric acid or a hydroxide of an alkali metal or an alkaline earth metal such as sodium hydroxide, potassium hydroxide or barium hydroxide, a carbonic acid salt of an alkali metal or an alkaline earth metal such as sodium carbonate, potassium carbonate or calcium carbonate. In general, the reaction may be conveniently carried out under basic conditions. The reaction may be carried out in the presence or absence of a solvent. Yet, the use of a solvent is preferred in order to carry out the reaction smoothly. The solvents to be employed are not limited so far as these are inert to the reaction, and preferably are, for instance, water and mixed solvents of water with alcohols such as methanol and ethanol or with ethers such as tetrahydrofuran and dioxane. The reaction temperature is not specifically limited, but temperatures between room temperature and the reflux temperature may be preferred.

After completion of the reaction, the desired compound may be taken out of the reaction mixture according to a usual way. For example, it is obtained by extracting the reaction mixture after addition of an adequate organic solvent, and evaporating the solvent from the resulting extract. The desired compound thus obtained may, if needed, be further purified by a conventional method, for example, column chromatography and thin layer chromatography.

The compound having the aforementioned general formula (II) which is a starting material used in conducting the process of the present invention is a novel compound, and may be, for instance, prepared according to the following process.

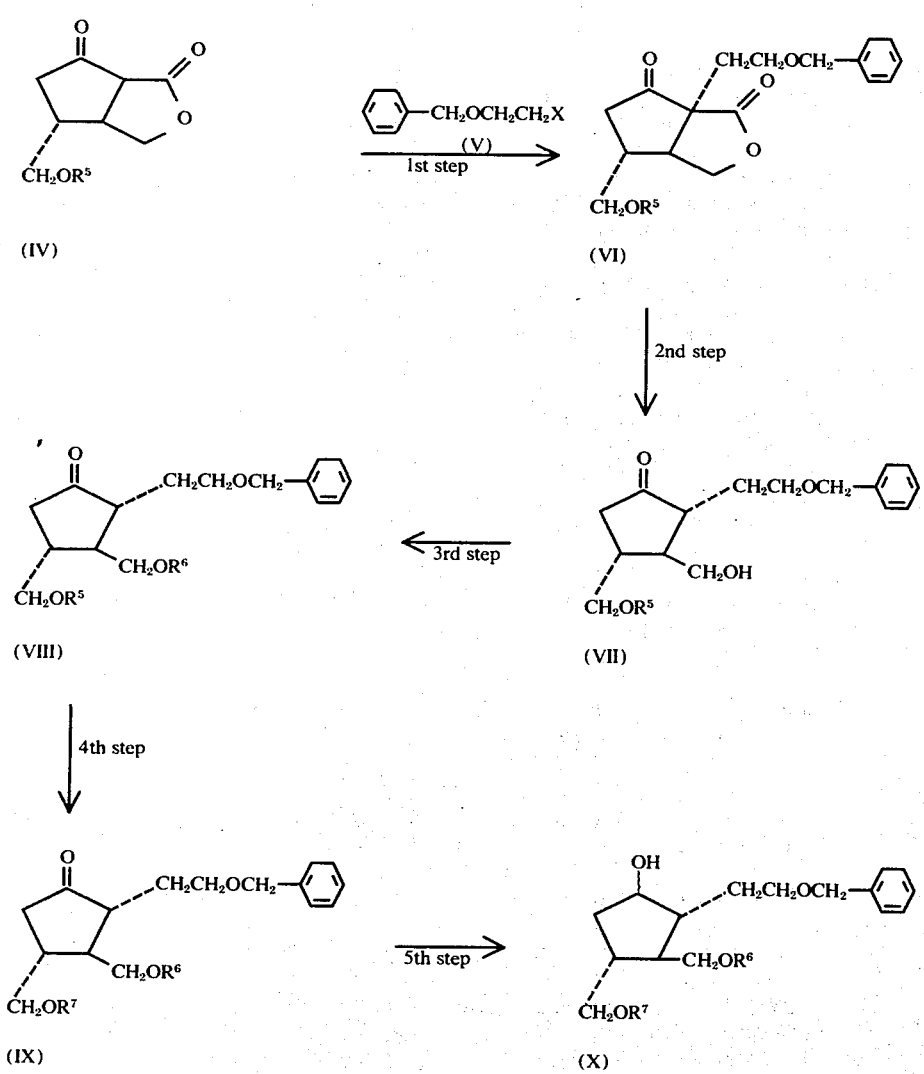

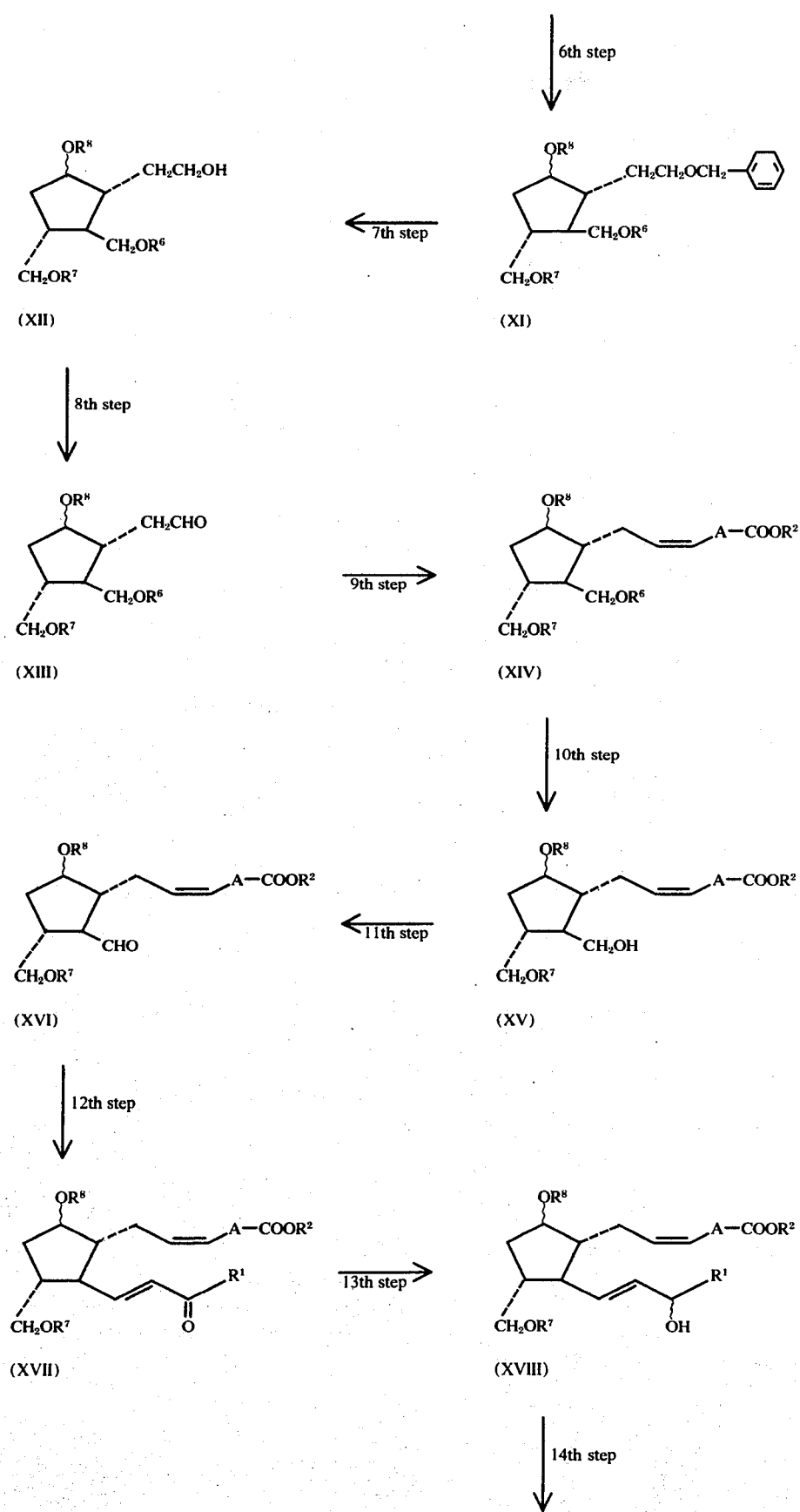

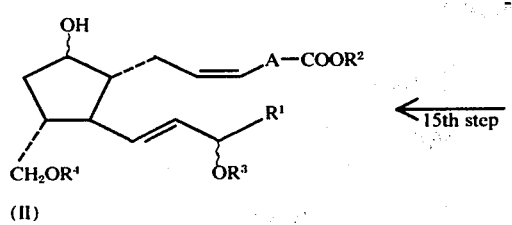

(II)

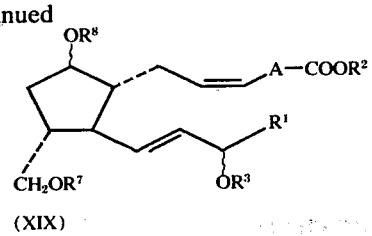

(XIX)

In the above formulae, A, $R^1$, $R^2$, $R^3$ and $R^4$ have the meanings defined above, $R^5$ represents an alkoxycarbonyl group and $R^6$, $R^7$ and $R^8$ represent protecting groups for the hydroxyl groups. The protecting group for the hydroxyl group is not limited so far as the reaction for removing the employed protecting group and replacing by a hydrogen atom which will be conducted later does not affect other parts of the compound, and may be exemplified by the same groups as in $R^3$ and $R^4$. $R^7$ and $R^8$ of the protecting groups for the hydroxyl groups are groups which are not removed at the time when $R^6$ of the protecting group for the hydroxyl group is removed in the later 10th step. $R^3$ of the protecting group for the hydroxyl group is a group which is not removed at the time when $R^8$ of the protecting group for the hydroxyl group is removed in the later 15th step. X represents a halogen atom such as chlorine, bromine or iodine.

The starting compounds having the formula (IV) may be prepared by the process described in our German Patent Offenlegungsschift No. 2,344,059.

Each step will be illustrated below.

The 1st step is directed to the preparation of the compound having the aforementioned general formula (VI) and achieved by bringing the compound having the aforementioned general formula (IV) into contact with the compound having the aforementioned general formula (V). The reaction may be carried out in the presence of a base. The bases to be conveniently employed may be exemplified by strong bases, for instance, alkali metals such as metallic sodium, hydrides of alkali metals and alkaline earth metals such as sodium hydride, potassium hydride and calcium hydride and alkoxides of alkali metals and alkaline earth metals such as sodium methoxide, potassium ethoxide, potassium tert-butoxide and calcium ethoxide. Generally the reaction is conveniently carried out in the presence of a solvent. The solvents to be employed are not limited so far as these are inert to the reaction, and preferably are hydrocarbons such as benzene and toluene, ethers such as diethyl ether, tetrahydrofuran and dioxane and dialkyl sulfoxides such as dimethylsulfoxide, and these solvents in anhydrous state are especially preferred. Further, the reaction may preferably be conducted in an inert gas such as nitrogen, argon or helium. The reaction temperature is not specifically limited, but temperatures below room temperature may usually be preferred.

The 2nd step is directed to the preparation of the compound having the aforementioned general formula (VII) and achieved by bringing the compound having the aforementioned general formula (VI) into contact with a base. The bases to be conveniently employed may be exemplified by hydroxides of alkali metals and alkaline earth metals such as sodium hydroxide, potassium hydroxide and calcium oxide, carbonic acid salts of alkali metals and alkaline earth metals such as sodium carbonate, potassium carbonate and calcium carbonate, acetates of alkali metals and alkaline earth metals such as sodium acetate, potassium acetate and calcium acetate and organic bases such as pyridine, picoline and triethylamine. The reaction may be carried out in the presence or absence of a solvent. Yet, the use of a solvent is preferred in order to carry out the reaction smoothly. The solvents to be conveniently employed may be exemplified by water, alcohols such as methanol and ethanol, ethers such as tetrahydrofuran and dioxane, dialkyl sulfoxides such as dimethylsulfoxide, hexamethylphosphoroamide and mixed solvents of water with these organic solvents. The reaction may preferably be conducted in an inert gas such as nitrogen, argon or helium. The reaction temperature is not specifically limited, and generally is between room temperature and the reflux temperature of the solvent employed.

The 3rd step is directed to the preparation of the compound having the aforementioned general formula (VIII) and achieved by protecting the hydroxyl group of the compound having the aforementioned general formula (VII). The reaction is accomplished by bringing the said compound into contact with a usual compound capable of forming a protecting group for a hydroxyl group. The compounds to be employed may be exemplified by heterocyclic compounds such as dihydropyran, dihydrothiopyran, dihydrothiophene and 4-methoxy-5,6-dihydro-(2H)pyran, alkoxy halogenated hydrocarbons such as methoxymethylene chloride and ethoxyethylene chloride, unsaturated compounds such as ethyl vinyl ether and methoxy-1-cyclohexene, halogenated hydrocarbons such as methyl chloride and ethyl chloride, silane compounds such as hexamethylsilazane, alkoxy carbonyl halides such as benzyloxycarbonyl chloride and ethoxycarbonyl chloride, organic acids such as acetic acid, propionic acid, benzoic acid and p-phenylbenzoic acid or active derivatives of these organic acids such as acid anhydrides and acid chlorides. In cases where a heterocyclic compound or a unsaturated compound is employed, the reaction may be conducted in the presence of a small amount of an acid, for example, a mineral acid such as hydrochloric acid or hydrobromic acid or an organic acid such as picric acid, trifluoroacetic acid, benzenesulfonic acid or p-toluenesulfonic acid. The reaction may be carried out in the presence or absence of a solvent. Yet, the use of a solvent is preferred in order to carry out the reaction smoothly. The solvents to be employed are not limited so far as these are inert to the reaction, and preferably are inert organic solvents, for instance, hydrocarbons such as benzene and toluene, halogenated hydrocarbons such as chloroform and dichloromethane and nitriles such as acetonitrile. In cases where an alkoxy halogenated hydrocarbon, a halogenated hydrocarbon or silane compound is employed, the reaction is carried out in the presence of a base. The base to be used in the case of employing an alkoxy halogenated hydrocarbon or a halogenated hydrocarbon as the compound capable of forming the protecting group may be exemplified by a hydride of an alkali metal such as sodium hydride, potassium hydride or lithium hydride, an amide of an alkali metal such as sodium amide or potassium amide, an alkoxide of an alkali metal such as sodium alkoxide or potassium alkoxide or a metal salt of a dialkylsulfoxide such as a sodium or potassium salt of dimethylsulfoxide. In case of using a silane compound, it may be exemplified by a tertiary amine such as trimethylamine, triethylamine or pyridine. The reaction may be carried out in the presence or absence of a solvent. Yet, the use of a solvent is preferred in order to carry out the reaction smoothly. The solvents to be employed are not limited so far as these are inert to the reaction, and preferably are inert organic solvents, for instance, ethers such as tetrahydrofuran, dioxane and diethyl ether, hydrocarbons such as benzene, toluene and cyclohexane, dialkylformamide such as dimethylformamide and dialkyl sulfoxides such as dimethyl sulfoxide. In case of employing an alkoxycarbonyl halide, the reaction is also conducted in the presence of a base. The bases to be employed may be exemplified by carbonic acid salts of alkali metals and alkaline earth metals such as sodium carbonate, potassium carbonate and calcium carbonate, hydrogen carbonic acid salts of alkali metals and alkaline earth metals such as sodium hydrogen carbonate, potassium hydrogen carbonate and calcium hydrogen carbonate, tertiary organic bases such as triethylamine, pyridine and N-methylpiperazine, alkoxides of alkali metals and alkaline earth metals such as sodium methoxide, potassium methoxide and calcium ethoxide, hydrides of alkali metals and alkaline earth metals such as sodium hydride, potassium hydride and calcium hydride and alkali metals such as metallic sodium. Generally organic bases may be conveniently used. The reaction may be carried out in the presence or absence of a solvent. Yet, the use of a solvent is preferred in order to carry out the reaction smoothly. The solvent to solvents used may be exemplified by hydrocarbons such as benzene and toluene and ethers such as diethyl ether, tetrahydrofuran and dioxane. In case of using an excess amount of the organic base, other solvent may not be needed. The reaction employing an organic acid or its active derivative may be conducted in the absence of a solvent or in the presence of such solvent as an amine such as pyridine or triethylamine, a halogenated hydrocarbon such as chloroform or dichloromethane, an ether such as diethyl ether, tetrahydrofuran or dioxane, a hydrocarbon such as benzene or toluene or an ester such as ethyl acetate. The reaction temperature is not specifically limited, but is generally preferred to be between 0° C and room temperature.

The 4th step is directed to the preparation of the compound having the aforementioned general formula (IX), and this step takes place when the need arises. In case where the protecting group $R^5$ for the hydroxyl group of the compound having the aforementioned general formula (VIII) is one which may be removed at the time when the protecting group $R^6$ for the hydroxyl group is removed in the later 10th step, the protecting group $R^5$ for the hydroxyl group ought to be changed into another protecting group for a hydroxyl group which cannot be removed in the step. In cases where the protecting group $R^5$ is one which cannot be removed at the time when the protecting group $R^6$ for the hydroxy group is removed in the 10th step, the said protecting group $R^5$ may also be changed into another more preferable protecting group for a hydroxyl group, if desired. For example, if the protecting group $R^5$ for the hydroxyl group is an ethoxycarbonyl group and this group ought to be changed into an acetyl group being more preferable as a protecting group for a hydroxyl group, the object may be accomplished by firstly bringing the compound into contact with a base such as potassium hydroxide to remove the ethoxycarbonyl group therefrom and bringing the resultant into contact with acetic anhydride in the presence of, for instance, pyridine.

The 5th step is directed to the preparation of the compound having the aforementioned general formula (X), and achieved by converting the carbonyl group of the compound having the aforementioned general formula (IX) into a hydroxyl group by means of reduction. The reaction may be carried out in the presence or absence of a solvent by the use of a reducing agent. The reducing agents to be employed are not limited so far as these are reducing agents capable of converting carbonyl groups into hydroxyl groups, and may be preferably exemplified by metal hydrides such as sodium boron hydride, potassium boron hydride, lithium boron hydride, zinc boron hydride, lithium tri-tert-butoxyaluminum hydride, lithium trimethoxyaluminum hydride, sodium cyanoboron hydride and lithium 9b-boraperhydrophenalene hydride. The reaction may be carried out in the presence or absence of a solvent, but the use of a solvent is preferred in order to carry out the reaction smoothly. The solvents to be employed are not limited so far as these are inert to the reaction and may preferably be inert organic solvents, for instance, alcohols such as methanol, ethanol and isopropanol and ethers such as tetrahydrofuran and dioxane. The reaction temperature is not limited, but relatively lower temperatures may be preferred so as to avoid side reactions. Generally the preferable temperature is between −10° C and room temperature.

The 6th step is directed to the preparation of the compound having the aforementioned general formula (XI) and achieved by protecting the hydroxyl group of the compound having the aforementioned general formula (X). The protecting groups are not limited so far as these cannot be removed at the time when the protecting group $R^6$ for the hydroxyl group is removed later on. The reaction may be carried out by bringing the compound into contact with the compound capable of forming a protecting group for a hydroxyl group. The compound to be employed in order to form the protecting group and its reaction conditions are the same as described in the aforementioned 3rd step.

The 7th step is directed to the preparation of the compound having the aforementioned general formula (XII) and achieved by removing the benzyl group of the compound having the aforementioned general formula (XI). The reaction may be carried out in the presence of a catalyst through catalytic reduction. As the catalyst to be used, catalysts usually employed in catalytic reduction are freely used. Such catalyst may be exemplified by platinum oxide, Raney nickel and palladium-carbon. The reaction may generally be carried out in the presence of a solvent. The solvents to be employed are not limited so far as these are inert to the reaction, and may preferably be, for instance, alcohols such as methanol, ethanol and ethylene glycol, ethers such as diethyl ether, dioxane, tetrahydrofuran and diglyme, hydrocarbons such as benzene, toluene, cyclohexane and methylcyclohexane, esters such as ethyl acetate, organic acids such as acetic acid and dialkylformamide such as dimethylformamide. The reaction may be performed at atmospheric pressure or higher pressure. The reaction temperature is not limited, but a relatively lower temperature may be preferred so as to avoid side reactions. Generally it may preferably be between 0° C and room temperature.

The 8th step is directed to the preparation of the compound having the aforementioned general formula (XIII), and achieved by oxidizing the compound having the aforementioned general formula (XII). The reaction may be carried out in the presence of an oxidizing agent. The oxidizing agents to be preferably employed may be exemplified by chromic acids such as chromic acid, chromic anhydride, a chromic anhydride - pyridine complex (Collins reagent), chromic anhydride - conc. sulfuric acid - water (Jones reagent), sodium bichromate and potassium bichromate, organic active halogen compounds such as N-bromoacetamide, N-bromosuccinimide, N-bromophthalimide and N-chloro-p-toluenesulfonamide and N-chlorobenzenesulfonamide, aluminum alkoxides such as aluminum tert-butoxide and aluminum isopropoxide, dimethylsulfoxide - dicyclohexylcarbodiimide and dimethylsulfoxide - acetic anhydride. The solvents to be employed are not limited so far as these are inert to the reaction, and may preferably be, for instance, organic acids or mixtures of organic acids with organic acid anhydrides such as acetic acid and acetic acid - acetic anhydride and halogenated hydrocarbons such as dichloromethane, chloroform and carbon tetrachloride. In the cases of using active organic halides, aqueous organic solvents such as aqueous tert-butanol, aqueous acetone and aqueous pyridine are preferred. In the cases of using aluminum alkoxides, aromatic hydrocarbon such as benzene, toluene and xylene are preferred. In the case of using dimethylsulfoxide - dicyclohexylcarbodiimide or dimethylsulfoxide - acetic anhydride, other solvents are not necessary so far as an excess amount of dimethylsulfoxide is employed. In the cases of using aluminum alkoxides, it is preferred to use as a hydrogen acceptor an excess amount of a ketone such as acetone, methyl ethyl ketone, cyclohexanone or benzoquinone in addition to the above-mentioned solvents. In this reaction, it is needed to expel water completely from the reaction system. In the case of using dimethylsulfoxide - dicyclohexylcarbodiimide, a catalytic amount of an acid such as phosphoric acid or acetic anhydride is employed according to a conventional method. In the present reaction, chromic acids, particularly the chromic anhydride - pyridine complex (Collins reagent) and the chromic anhydride - conc. sulfuric acid - water (Jones reagent), are employed as the preferred oxidizing agents. The reaction temperature is not specifically limited, but a relatively lower temperature is preferred so as to avoid side reactions. Generally it is between −20° C and room temperature and preferably between 0° C and room temperature.

The 9th step is directed to the preparation of the compound having the aforementioned general formula (XIV), and achieved by reacting the compound having the aforementioned general formula (XIII) with a Witting reagent having the general formula:

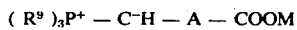  (XX)

wherein A is the same as above, $R^9$ represents a hydrocarbon group such as an aryl group, e.g., phenyl, or an alkyl group, e.g., n-butyl, and M represents an alkali metal such as sodium or potassium and subsequently treating the resultant reaction mixture with an acid to convert it into the free acid, and, if required, protecting the carboxyl group of the compound thus obtained. The Wittig reaction step for the reaction of the compound having the aforementioned general formula (XIII) with the compound having the aforementioned general formula (XX) is generally carried out by reacting the compound having the aforementioned general formula (XX) with the compound having the aforementioned general formula (XIII) in a molar ratio of 1 − 20:1, usually in the presence of a solvent and preferably by the use of an excess amount of Wittig reagent. As the solvents to be used, solvents employed in the usual Wittig reaction are freely employed. Such solvents may be inert organic solvents exemplified by ethers such as diethyl ether, tetrahydrofuran and dioxane, hydrocarbons such as benzene, toluene and hexane, dialkylsulfoxides such as dimethylsulfoxide, dialkylformamides such as dimethylformamide and halogenated hydrocarbons such as dichloromethane and chloroform. The reaction may preferably be carried out in an inert gas such as nitrogen, argon or helium. The reaction temperature is not specifically limited, but it may be between 0° C and the reflux temperature of the solvent. Room temperature is generally preferred. The products obtained by the above Wittig reaction are salts which can be readily converted into the free acids by the treatment with, for instance, organic acids such as acetic acid, propionic acid and oxalic and mineral acids such as hydrochloric acid and hydrobomic acid.

The carboxyl group of the compound thus obtained may be protected, if the need arises. If the carboxyl group is protected, the separation of the isomers to be required in the later stage can be smoothly conducted. The reaction may be carried out by bringing the compound into contact with the compound capable of forming a protecting group. The compounds to be used for forming the protecting groups may be exemplified by diazo hydrocarbons such as diazomethane, diazoethane, diazo-n-propane, diazo-n-butane, diazoisobutane, diazo-n-octane, 1-diazo-2-ethylhexane, 1-diazo-2-propene, cyclohexyldiazomethane and phenyldiazomethane, halogenated alcohols such as 2,2,2-trichloroethanol and heterocyclic compounds such as dihydropyran, dihydrothipyran, dihydrothiophene and 4-methoxy-5,6-dihydro-(2H)pyran. The solvents to be used in the cases of using diazo hydrocarbons are not limited so far as these are inert to the reaction, and may preferably be, for instance, ethers such as diethyl ether and dioxane. The reaction temperature is not specifically limited, but a relatively lower temperature is preferred so as to avoid side reactions and to prohibit decomposition of the diazo hydrocarbons. Generally, the reaction may preferably be conducted under ice-cooling. In the cases of using halogenated alcohols such as 2,2,2-trichloroethanol, the reaction is preferably carried out in the presence of a dehydrating agent such as sulfuric acid or dicyclohexylcarbodiimide. The reaction may be carried out in the presence or absence of a solvent, but the use of a solvent is preferred so as to perform the reaction smoothly. The solvents to be used are not limited so far as these are inert to the reaction, and may preferably be, for instance, ethers such as diethyl ether and dioxane. The reaction temperature is not specifically limited, but room temperature is generally preferred. In the case of using a heterocyclic compound, the reaction may be performed in the presence of a small amount of an acid, for instance, a mineral acid such as hydrochloric acid or hydrobromic acid or an organic acid such as picric acid, trifluoroacetic acid, benzenesulfonic acid or p-toluenesulfonic acid. The reaction may be carried out in the presence or absence of a solvent. Yet, the use of a solvent is preferred so as to perform the reaction smoothly. The solvents to be used are not limited so far as these are inert to the reaction, and may preferably be inert organic solvents such as halogenated hydrocarbons, for instance, chloroform and dichloromethane and nitriles, for instance, acetonitrile. The reaction temperature is not specifically limited, but may be between room temperature and the reflux temperature of the solvent. Room temperature is most preferred.

The 10th step is directed to the preparation of the compound having the aforementioned general formula (XV), and achieved by removing the protecting group $R^6$ for the hydroxyl group from the compound having the aforementioned general formula (XIV). The removing reaction condition varies with the kind of the protecting group. In cases where the protecting groups are heterocyclic groups such as 2-tetrahydropyranyl, 2-tetrahydrothiopyranyl, 2-tetrahydrothienyl and 4-methoxytetrahydropyran-4-yl or alkoxy hydrocarbon groups such as methoxymethyl, ethoxymethyl, 1-ethoxyethyl and 1-methoxycyclohexane-1-yl, the reactions may be readily accomplished by bringing the compounds into contact with acids. The acids to be employed preferably are, for instance, organic acid such as formic acid, acetic acid, propionic acid, butyric acid, oxalic acid and malonic acid or mineral acids such as hydrochloric acid, hydrobromic acid and sulfuric acid. The reaction may be carried out in the presence or absence of a solvent. Yet, the use of a solvent is preferred so as to perform the reaction smoothly. The solvents to be used are not limited so far as these are inert to the reaction, and may preferably be, for instance, water, alcohols such as methanol and ethanol, ethers such as tetrahydrofuran and dioxane or mixed solvents of water with these organic solvents. The reaction temperature is not specifically limited, and may be between room temperature and the reflux temperature of the solvent. Room temperature is most preferred. In case where the protecting group for the hydroxyl group is a hydrocarbon group such as methyl or ethyl, the reaction may be accomplished by bringing the compound into contact with a halogenated boron compound such as boron trichloride or boron tribromide. The reaction may be conducted in the presence or absence of a solvent. Yet, the use of a solvent is preferred so as to carry out the reaction smoothly. The solvents to be employed are not limited so far as these are inert to the reaction, and may preferably be, for instance, halogenated hydrocarbons such as dichloromethane and chloroform. The reaction temperature is not specifically limited, but a relatively lower temperature is preferred so as to avoid side reactions. Temperatures in the range of from $-30°$ C to room temperature are preferred. In case where the protecting group for the hydroxyl group is, for instance, an alkylsilyl group such as trimethylsilyl, the reaction may be easily accomplished by bringing the compound into contact with water or with water containing an acid. The acids to be contained in the water containing an acid may be any of organic acids such as formic acid, acetic acid, propionic acid, butyric acid, oxalic acid and malonic acid or mineral acids such as hydrochloric acid, hydrobromic acid and sulfuric acid. The reaction may be performed in the presence or absence of a solvent. If an excess amount of water is employed, other solvents are not necessarily required. The other solvents mentioned above may preferably be the mixed solvents of water with organic solvents such as ethers, e.g., tetrahydrofuran and dioxane or alcohols, e.g., methanol and ethanol. The reaction temperature is not specifically limited, but may preferably be between about room temperature and 60° C. In cases where the protecting group for the hydroxyl group is, for instance, a carbonic acid residue of an ester such as benzyloxycarbonyl or ethoxycarbonyl or an acyl group such as acetyl, propionyl, benzoyl or p-phenylbenzoyl, the reaction may be easily accomplished by bringing the compound into contact with an acid or a base. The acids or bases to be employed may preferably be, for instance, mineral acids such as hydrochloric acid, hydrobromic acid and sulfuric acid, hydroxides of alkali metals and alkaline earth metals such as sodium hydroxide, potassium hydroxide and calcium hydroxide or carbonic acid salts of alkali metals and alkaline earth metals such as sodium carbonate, potassium carbonate and calcium carbonate. Generally, the reaction may preferably be carried out under basic conditions. The reaction may be conducted in the presence or absence of a solvent. Yet, the use of a solvent is preferred so as to carry out the reaction smoothly. The solvents to be employed are not limited so far as these are inert to the reaction, and may preferably be, for instance, water, alcohols such as methanol and ethanol, ethers such as tetrahydrofuran and dioxane or mixed solvents of water with these organic solvents. The reaction temperature is not specifically limited, but may be between room temperature and the reflux temperature of the solvent.

The 11th step is directed to the preparation of the compound having the aforementioned general formula (XVI), and achieved by oxidizing the compound having the aforementioned general formula (XV). The reaction is performed in the presence of an oxidizing agent. The oxidizing agents and their reaction conditions are the same as mentioned in the aforementioned 8th step.

The 12th step is directed to the preparation of the compound having the aforementioned general formula (XVII), and achieved by reacting the compound having the aforementioned general formula (XVI) with a Wittig reagent having the general formula:

 (XXI)

wherein $R^1$ has the significance defined before and $R^{10}$ represents a hydrocarbon group such as an aryl group, e.g., phenyl, or an alkyl group, e.g., n-butyl. The reaction conditions of the present step are the same as mentioned in the aforementioned 9th step.

The 13th step is directed to the preparation of the compound having the aforementioned general formula (XVIII), and achieved by reducing the compound having the aforementioned general formula (XVII). The reaction may be performed in the presence or absence of a solvent by using a reducing agent. The reducing agents to be used are not limited so far as these are capable of converting a carbonyl group into a hydroxyl group without reduction of a double bond. Such reducing agents are preferably exemplified by hydrogenated metal compounds such as sodium boron hydride, potassium boron hydride, lithium boron hydride, zinc boron hydride, lithium tri-tert-butoxyaluminum hydride, lithium trimethoxyaluminum hydride, sodium cyanoboron hydride and lithium 9b-boraperhydrophenalene hydride. The reaction may be conducted in the presence or absence of a solvent. Yet, the use of a solvent is preferred so as to carry out the reaction smoothly. The solvents to be used are not limited so far as these are inert to the reaction, and may preferably be inert organic solvents exemplified by alcohols such as methanol, ethanol and isopropanol or ethers such as tetrahydrofuran and dioxane. The reaction temperature is not specifically limited, but a relatively lower temperature is preferred so as to avoid side reactions. Generally, temperatures in the range of from −10° C to room temperature are preferred.

The 14th step is directed to the preparation of the compound having the aforementioned general formula (XIX), and achieved by protecting the hydroxyl group of the compound having the aforementioned general formula (XVIII). The protecting groups to be employed are not limited so far as these cannot be simultaneously removed at the time when the protecting group $R^8$ for the hydroxyl group is removed in the later 15 step. The reaction may be accomplished by bringing the compound into contact with the compound capable of forming a protecting group for the hydroxyl group. The compound capable of forming a protecting group for the hydroxyl group to be used and the reaction conditions are the same as mentioned in the aforementioned 3rd step.

The 15th step is directed to the preparation of the compound having the aforementioned general formula (II), and achieved by removing the protecting group $R^8$ for the hydroxyl group from the compound having the aforementioned general formula (XIX) and then, if the protecting group $R^7$ is simultaneously removed to let the hydroxyl group free, protecting the hydroxyl group again. The reaction conditions in the reaction for removing the protecting group $R^8$ for the hydroxyl group vary with the kind of the protecting group for the hydroxyl group. The reaction conditions which depend upon the kind of the protecting group for the hydroxyl group are the same as described in the aforementioned 10th step.

As outlined above, where the protecting group $R^8$ for the hydroxyl group of the compound having the aforementioned general formula (XIX) is removed, the protecting group $R^7$ for the hydroxyl group thereof can be simultaneously removed depending upon the kind of the protecting group $R^7$. In this case, one is converted into a secondary hydroxyl group and the other into a primary hydroxyl group. Further, where the secondary hydroxy group is oxidized in the later step, the primary hydroxyl group if affected by the reaction. Therefore, in cases where the protecting group $R^8$ for the hydroxyl group is to be removed and the reaction for the removal also removes the protecting group $R^7$ for the hydroxyl group to make the hydroxyl group naked, the primary hydroxyl group ought to be protected again. The compound forming the protecting group for the hydroxyl group is not limited so far as the compound is a usual one capable of protecting a primary hydroxyl group without affecting a secondary hydroxyl group, and may preferably be exemplified by an organic acid such as acetic acid, propionic acid, benzoid acid, p-phenylbenzoic acid, trichloroacetic acid or trifluoroacetic acid, an active derivative of the organic acid such as an acid anhydride or an acid halide or a trityl compound such as trityl chloride. The reacton may be carried out in the presence of a base. The bases to be employed preferably are organic bases such as triethylamine and pyridine. The reaction may be conducted in the presence or absence of a solvent. The solvents to be used in the cases of employing solvents may be exemplified by halogenated hydrocarbons such as chloroform and dichloromethane, ethers such as diethyl ether, tetrahydrofuran and dioxane, hydrocarbons such as benzene and toluene and esters such as ethyl acetate. The reaction temperature is not specifically limited, but a relatively lower temperature is preferred so as to avoid side reactions. Generally, temperatures in the range of from −80° C to room temperature are preferred.

After completion of the reactions, the desired compounds of these steps are taken out of the reaction mixtures in a usual way. If the need arises, the desired compounds obtained above can be further purified by the use of a conventional manner, for instance, column chromatography, thin layer chromatography, and the like.

In cases where the desired compounds thus obtained in the aforementioned steps are mixtures of optical isomers, these can be separated and resolved in a convenient synthesis step.

The following examples and reference examples will concretely illustrate the process of the present invention.

EXAMPLE 1

9-Oxo-11α-hydroxymethyl-15 -hydroxyprosta-5(cis),13(trans)-dienoic acid and
9-oxo-11α-hydroxymethyl-15β-hydroxyprosta-5(cis),13-(trans)-dienoic acid

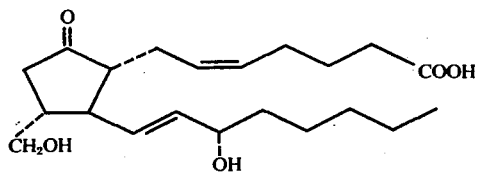 and 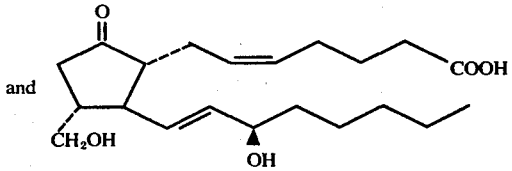

1. In 20 ml of dichloromethane was dissolved 352 mg of 9-hydroxy-11α-tri-chloroacetyloxymethyl-15-(2-tetrahydropyranyl)-oxyprosta-5(cis),13(trans)-dienoic acid methyl ester. To this solution was added 1.34 g of a chromic anhydride, - pyridine complex (Collins reagent) and the resulting mixture was stirred for 30 minutes under ice-cooling. After completion of the reaction, to the reaction mixture was added ether and this was subsequently filtered by Hyflo Super Cel (Johns Manville Sales Corp. U.S.A.). The filtrate was successively washed under ice-cooling with a cooled 2% aqueous sodium carbonate solution, a cooled 1% aqueous hydrochloric acid solution, a cooled 5% aqueous sodium hydrogen carbonate solution and a saturated aqueous sodium chloride solution, and dried over anhydrous sodium sulfate. Upon removal of the solvent from the solution by vacuum evaporation at low temperature, there was obtained 330 mg of an oily substance. The obtained substance was purified by means of column chromatography employing 2.3 g of silica gel. The portions eluted with benzene ~ benzene - ethyl acetate (95 : 5) were collected. Upon evaporation of the solvent from the eluate, there was obtained 229 mg of 9-oxo-11α trichloroacetyloxymethyl-15-(2-tetrahydropyuranyl)oxyprosta-5(cis),13(trans)-dienoic acid methyl ester.

IR spectrum (liquid film) $v_{max}cm^{-1}$: 1771, 1745, 1436, 1240, 1159, 1111, 1073, 1019, 981, 823.

NMR spectrum (CDCl$_3$) δ : ppm 0.69 – 1.06 (3H, triplet), .06 – 2.88 (27H, multiplet), 3.68 (3H, singlet), 3.17 – 4.30 (3H, multiplet), 4.30 – 4.54 (2H, multiplet), 4.54 – 4.76 (1H, multiplet), 5.18 – 5.70 (4H, multiplet).

In a mixture solution of 3.0 ml of acetic acid, 3.0 ml of water and 0.4 ml of tetrahydrofuran was dissolved 276 mg of 9-oxo-11α -trichloroacetyloxymethyl-15-(2:tetrahydropyranyl) oxyprosta-5-(cis),13(trans)-dienoic acid methylester and the resulting solution was stirred at 45° C for 4 hours. After completion of the reaction, to the reaction mixture was added ice-water and subsequently ethyl acetate, whereby extraction was carried out. The extract was washed with a saturated aqueous sodium chloride solution, and then dried over anhydrous sodium sulfate. Upon evaporation of the solvent from the extract, there was obtained 280 mg of an oily substance. The obtained substance was purified by means of column chromatography employing 2.5 g of silica gel having been washed with an aqueous hydrochloric acid. The portions eluted with benzene - ether (99 : 1 to 90 : 10) were collected. Upon evaporation of the solvent from the eluate, there was obtained 230 mg of 9-oxo-11α-trichloroacetyloxymethyl-15-hydroxyprosta-5(cis),13(trans)-dienoic acid methyl ester as an oil.

IR spectrum (liquid film) $v_{max}cm^{-1}$: 3440, 1768, 1740, 1436, 1239, 1012, 978, 822.

In 4 ml of anhydrous methanol was dissolved 230 mg of 9-oxo-11α-trichloroacetyloxymethyl-15-hydroxyprosta-5(cis), 13(trans)-dienoic acid methylester. To this solution was added 50 mg of anhydrous potassium carbonate, and the mixture was stirred at room temperature for 45 minutes. After completion of the reaction mixture was poured into a mixture solvent of ice-water and acetic acid, and ether was added to this mixture, whereby extraction was carried out. The extract was washed with a saturated aqueous sodium chloride solution, and dried over anhydrous sodium sulfate. Upon evaporation of the solvent from the extract, there was obtained 226 mg of an oily substance. The obtained substance was purified by means of column chromatography employing 2.2 g of silica gel having been washed with an aqueous hydrochloric acid. The portions eluted with benzene - ethyl acetate (90 : 10 to 80 : 20) were collected. Upon evaporation of the solvent from the eluate, there was obtained 54 mg of 9-oxo-11-α-hydroxymethyl-15β-hydroxyprosta-5(cis), 13(trans)-dienoic acid methylester as an oil. The portions further eluted with benzene- ethyl acetate (80 : 20 ) were also collected. Upon evaporation of the solvent from the eluate, there was obtained 41 mg of a mixture of 9-oxo-11α-hydroxymethyl-15βB-hydroxyprosta-5-(cis),13(-trans)-dienoic acid methylester and 9-oxo-11α-hydroxymethyl-15α-hydroxyprosta-5-(cis),13(trans)-dienoic acid methylester as an oil. Furthermore, the portions eluted with benzene - ethyl acetate (50 : 50) were collected. Upon evaporation of the solvent from the eluate, there was obtained 72.5 mg of 9-oxo-11α-hydroxymethyl-15α-hydroxyprosta-5(cis),13(trans)-dienoic acid methylester.

The result obtained with thin layer chromatography showed that 9-oxo-11α-hydroxymethyl-15α-hydroxyprosta-5-(cis),13(trans)-dienoic acid methylester is somewhat higher in polarity than 9-oxo-11α-hydroxymethyl-15α-hydroxyprosta-5-(cis),13(trans)-dienoic acid methylester.

Their IR spectra and NMR spectra agreed with each other.

IR spectrum (CDCl) $v_{max}cm^{-1}$: 3430, 1735, 1438, 1370, 1240, 1159. 1052, 1019, 970.

In a mixture solution of 2.4 ml of methanol, 0.6 ml of water and 1.0 ml of a 10% aqueous potassium hydroxide solution was dissolved 72 mg of 9-oxo-11α-hydroxymethyl-15α-hydroxyprosta-5(cis),13(trans)-dienoic acid methylester. The resulting solution was stirred at room temprature for 3 hours. After completion of the reaction, the reaction mixture was poured into a mixture solvent of ice-water and acetic acid, and the mixture was extracted with ether. The extract was dried over anhydrous sodium sulfate. Upon evaporation of the solvent from the extract, there was obtained 73 mg of an oily substance. The obtained substance was purified by means of column chromatography employing silica gel having been washed with an aqueous hydrochloric acid solution. The portions eluted with benzene - ethyl acetate (65 : 35) were collected. Upon evaporation of the solvent from the eluate, there was obtained 48 mg of 9-oxo-11α-hydroxymethyl-15α-hydroxyprosta-5(cis), 13(trans)-dienoic acid.

According to the above procedure, 54 mg of 9-oxo-11α-hydroxymethyl-15β-hydroxyprosta-5-(cis),13(-trans)-dienoic acid methylester gave 46 mg of 9-oxo-11α-hydroxymethyl-15β-hydroxyprosta-5-(cis),13(-trans)-dienoic acid. Likewise, 41 mg of the mixture of 9-oxo-11α-hydroxymethyl-15α-hydroxyprosta-5(cis),13-(trans)-dienoic acid methylester and 9-oxo-11α-hydroxymethyl-15β-hydroxyprosta-5(cis),13(-trans)-dienoic acid methylester gave 36 mg of the mixture of 9-oxo-11α-hydroxymethyl-15α-hydroxyprosta-5-(cis),13(trans)-dienoic acid and 9-oxo-11α-hydroxymethyl-15-β-hydroxyprosta-5(cis), 13(trans)-dionoic acid.

Their IR spectra and NMR spectra agree with each other.

IR spectrum (liquid film) $v_{max}cm^{-1}$: 3400, 2940, 1722, 1703, 1400, 1230, 1160, 1053, 1018, 970.

NMR spectrum (CDCl$_3$) δ : ppm 0.66 – 1.10 (3H, multiplet), 1.10 – 1.90 (11H, multiplet), 1.90 – 2.60 (10H, multiplet), 3.18 – 4.32 (6H, multiplet), 5.26 – 5.76 (4H, multiplet)

2. In 25 ml of dichloromethane was dissolved 399 mg of 9-hydroxy-11α-trichloroacetyloxymethyl-15-(2-tetrahydropyranyl)-oxyprosta-5-(cis), 13(trans)-dienoic acid, and to this solution was then added 1.58 g of a chromic anhydride- pyridine complex. The mixture was stirred under ice-cooling for 30 minutes. After completion of the reaction, the reaction mixture was then treated in the same manner as in Example 1(1), except that the reaction mixture was successively washed twice with a saturated aqueous sodium chloride solution, a cooled 1 % aqueous hydrochloric acid solution and a saturated aqueous sodium chloride solution, to give 344 mg of 9-oxo-11α-trichloroacetyloxymethyl-15-(2-tetrahydropyranyl)oxyprosta-5(cis), 13(trans)-dienoic acid as oil.

IR spectrum (liquid film) $\nu_{max}cm^{-1}$: 1770, 1744, 1708.

NMR spectrum (CDCl$_3$) δ : ppm 5.22 – 5.70 (4H, multiplet).

In 5.0 ml of anhydrous methanol was dissolved 262 mg of 9-oxo-11α-trichloroacetyloxymethyl-15-(2-tetrahydropyranyl) oxyprosta-5(cis), 13(trans)-dienoic acid and to this was then added 70 mg of anhydrous potassium carbonate. The mixture was stirred at room temperature for 1 hour. After completion of the reaction, the reaction mixture was then treated in the same manner as in Example 1 to yield 191 mg of 9-oxo-11α-hydroxymethyl-15-(2-tetrahydropyranyl)oxyprosta-5(cis),13(trans)-dienoic acid as an oil.

IR spectrum (liquid film) $\nu_{max}cm^{-1}$: 3390, 1720, 1702.

NMR spectrum (CDCL$_3$) δ : ppm 5.25 – 5.78 (4H, multiplet).

In a mixture solution of 2 ml of acetic acid, 2 ml of water and 0.2 ml of tetrahydrofuran was dissolved 186 mg of 9-oxo-11α-hydroxymethyl-15-(2-tetrahydropyranyl)oxyprosta-5(cis),13(trans)-dienoic acid. The mixture was then stirred at a temperature of 45° C for 3.5 hours. After completion of the reaction, the reaction mixture was then treated in the same manner as in Example 1 to yield 45 mg of 9-oxo-11α-hydroxymethyl-15β-hydroxyprosta-5(cis),13(trans)-dienoic acid, 28 mg of 9-oxo-11α-hydroxymethyl-15α-hydroxyprosta-5(cis),13(trans)dienoic acid and 59 mg of the mixture thereof all as oils.

Their IR spectra and NMR spectra were the same as those in Example 1 (1).

EXAMPLE 2

9-Oxo-11α-hydroxymethyl-15α-hydroxyprosta-5(cis),13 (trans)-dienoic acid potassium salt In a mixture solution of 1.0 ml of methanol and 0.1 ml of water was dissolved 36.6 mg of 9-oxo-11α-hydroxymethyl-15α-hydroxyprosta-5(cis),13(trans)-dienoic acid and to this solution was then added 6.9 mg of potassium carbonate. The resulting mixture was stirred at room temperature for 1 hour. After completion of the reaction, the reaction mixture was subjected to vacuum evaporation of the solvent to give 40.4 mg of the desired compound as an oil.

IR spectrum (liquid film) $\nu_{max}cm^{-1}$: 3400, 1730, 1580 – 1560.

EXAMPLE 3

9-Oxo-11α-hydroxymethyl-15α-hydroxy-20-ethylprosta-5(cis),13(trans)-dienoic acid and
9-oxo-11α-hydroxymethyl-15β-hydroxy-20-ethylprosta-5(cis),13(trans)-dienoic acid

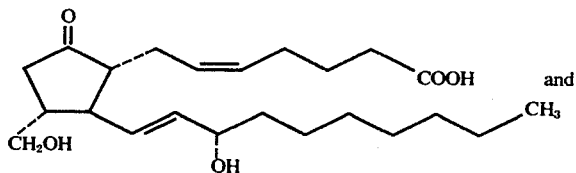
and
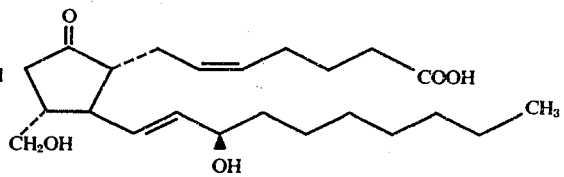

In 35 ml of anhydrous dichloromethane was dissolved 735 mg of 9-hydroxy-11α-trichloroacetyloxymethyl-15-(2-tetrahydropyranyl)oxy-20-ethylprosta-5(cis),13(trans)-dienoic acid methylester. To this solution was added 2.7 g of a chromic anhydride - pyridine complex, and the mixture was stirred for 30 minutes under ice-cooling. After completion of the reaction, the reaction mixture was then treated in the same manner as in example 1 to give 600 mg of 9-oxo-11α-trichloroacetyloxymethyl-15-(2-tetrahydropyranyl)oxy-20-ethylprosta-5(cis),13(trans)dienoic acid methylester as an oil.

IR spectrum (liquid film) $\nu_{max}cm^{-1}$: 1770, 1745, 1156, 1111, 1018.

NMR spectrum (CDCl$_3$) δ: ppm 0.87 (3H, multiplet), 3.68 (3H, singlet), 4.55 – 4.75 (1H, multiplet), 5.2 – 5.7 (4H, multiplet).

In a mixture solution of 6.0 ml of acetic acid, 6.0 ml of water and 0.8 ml of tetrahydrofuran was dissolved 585 mg of 9-oxo-11α-trichloroacetyloxymethyl-15-(2-tetrahydropyranyl)oxy20-ethylprosta-5(cis),13(trans)-dienoic acid methylester, and this solution was stirred at a temperature of 45° C for 4 hours. After completion of the reaction, the reaction mixture was then treated in the same manner as in example 1 to give 465 mg of 9-oxo-11α-trichloracetyloxymethyl-15-hydroxy-20-ethylprosta-5(cis),13(trans)-dienoic acid methylester as an oil.

IR spectrum (liquid film) $\nu_{max}cm^{-1}$: 3440, 1769, 1740, 1012.

In 8.0 ml of anhydrous methanol was dissolved 465 mg of 9-oxo-11α-trichloroacetyloxymethyl-15-hydroxy-20-ethylprosta-5(cis),13(trans)-dienoic acid methylester. To this solution was added 100 mg of anhydrous potassium carbonate, and this mixture was stirred at room temperature for 35 minutes. After completion of the reaction, the reaction mixture was then treated in the same manner as in example 1 to give 115 mg of 9-oxo-11α-hydroxymethyl-15β-hydroxy-20-ethylprosta-5(cis), 13(trans)-dienoic acid methylester, 98 mg of a mixture of 9-oxo-11α-hydroxymethyl-15β-hydroxy-20-ethylprosta-5(cis), 13(trans)-dienoic acid methylester and 9-oxo-11α-hydroxymethyl-15α-hydroxy-20-ethylprosta-5(cis),13(trans)-dienoic acid methylester and 140 mg of 9-oxo-11α-hydroxymethyl-15α-hydroxy-20-ethylprosta-5(cis),13(trans)-dienoic acid methylester.

IR spectra and NMR spectra of the products agreed with each other.

IR spectra (liquid film) $\nu_{max}cm^{-1}$: 3440, 1740.

NMR spectra (CDCl₃) δ: ppm 0.87 (3H, multiplet), 2.70 (2H, br. singlet), 3.60 (3H, singlet), 4.03 (1H, multiplet), 5.30 (2H, multiplet), 5.50 (2H, multiplet).

In a mixture solution of 4.2 ml of methanol, 1.05 ml of water and 1.7 ml of a 10% aqueous potassium hydroxide was dissolved 130 mg of 9-oxo-11α-hydroxymethyl-15α-hydroxy-20-ethylprosta-5(cis),13(trans)-dienoic acid methylester, and this solution was stirred at room temperature for 2 hours. After completion of the reaction, the reaction mixture was then treated in the same manner as in example 1 to give 82 mg of 9-oxo-11α-hydroxymethyl-15α-hydroxy-20-ethylprosta-5(cis),13(trans)-dienoic acid as an oil.

In the same manner as above, 110 mg of 9-oxo-11α-hydroxymethyl-15β-hydroxy-20-ethylprosta-5(cis),13(trans)dienoic acid methylester gave 74 mg of 9-oxo-11α-hydroxymethyl-15β-hydroxy-20-ethylprosta-5(cis),13(trans)-dienoic acid.

9-oxo-11α-hydroxymethyl-15α-hydroxy-20-ethylprosta5(cis),13(trans)-dienoic acid

IR spectrum (liquid film) ν maxcm⁻¹: 3400, 3400 - 2400, 1730.

NMR spectrum (CD₃COCD₃) δ: ppm 0.87 (3H, multiplet), 3.67 (2H, multiplet), 4.10 (1H, multiplet), 5.0 – 6.0 (7H, multiplet).

9-Oxo-11α-hydroxymethyl-15β-hydroxy-20-ethylprosta-5(cis),13(trans)-dienoic acid IR spectrum (liquid film) ν $_{max}$cm⁻¹: 3400, 3400 - 2400, 1730.

NMR spectrum (CD₃COCD₃) δ: ppm 0.87 (3H, multiplet), 3.67 (2H, multiplet), 4.11 (1H, multiplet), 5.40 and 5.63 (4H, multiplet), 6.06 (3H, br. singlet).

EXAMPLE 4

9-Oxo-11α-hydroxymethyl-15α-hydroxy-20-ethylprosta-5(cis),13(trans)-dienoic acid sodium salt In a mixture solution of 1.0 ml of methanol and 0.1 ml of water was dissolved 44 mg of 9-oxo-11α-hydroxymethyl-15αhydroxy-20-ethylprosta-5(cis),13(trans)-dienoic acid and to this solution was then added 9.0 mg of sodium carbonate. The resulting mixture was stirred at room temperature for 1.5 hours. After completion of the reaction, the reaction mixture was subjected to vacuum evaporation of the solvent to give 48 mg of the desired product as oil.

IR spectrum (liquid film) ν $_{max}$cm⁻¹: 3400, 1730, 1580 ~ 1560.

EXAMPLE 5

9-Oxo-11α-hydroxymethyl-15α-hydroxy-16,16-dimethylprosta-5(cis),13(trans)-dienoic acid and
9-oxo-11α-hyddroxymethyl-15β-hydroxy-16,16-dimethylprosta-5(cis),13(trans)-dienoic acid In 40 ml of anhydrous dichloromethane was dissolved 850 mg of 9-hydroxy-11α-trichloracetyloxymethyl-15-(2-tetrahydropyranyl)oxy-16,16-dimethylprosta-5(cis),13(trans)-dienoic acid methylester. To this solution was added 3.1 g of a chromic anhydride - pyridine complex, and the mixture was stirred for 30 minutes under ice-cooling. After completion of the reaction, the reaction mixture was then treated in the same manner as in example 1 to give 700 mg of 9-oxo-11α-trichloroacetyloxymethyl15-(2-tetrahydropyranyl)oxy-16,16-dimethylprosta-5(cis),13 (trans)-dienoic acid methylester as an oil.

IR spectrum (liquid film) ν $_{max}$cm⁻¹: 1770, 1742, 1110, 1018.

NMR spectrum (CDCl₃) δ: ppm 0.82, 0.90 and 0.94 (9H, singlet and multiplet), 3.68 (3H, singlet), 4.5 – 4.7 (1H, multiplet), 5.2 – 5.6 (4H, multiplet).

In a mixture solution of 7.0 ml of acetic acid, 7.0 ml of water and 0.9 ml of tetrahydrofuran was dissolved 690 mg of 9-oxo-11α-trichloroacetyloxymethyl-15-(2-tetrahydropyranyl)oxy-16,16-dimethylprosta-5(cis),13(trans)-dienoic acid methylester, and this solution was stirred at a temperature of 45° C for 4 hours. After completion of the reaction, the reaction mixture was then treated in the same manner as in example 1 to give 531 mg of 9-oxo-11α-trichloroacetyloxymethyl-15-hydroxy16,16-dimethylprosta-5(cis),13(trans)-dienoic acid methylester as an oil.

IR spectrum (liquid film) ν $_{max}$cm⁻¹: 3450, 1770, 1740, 1011.

In 9.0 ml of anhydrous methanol was dissolved 531 mg of 9-oxo-11α-trichloroacetyloxymethyl-15-hydroxy-16,16-dimethylprosta-5(cis),13(trans)-dienoic acid methylester. To this solution was added 115 mg of anhydrous potassium carbonate, and the mixture was stirred at room temperature for 30 minutes. After completion of the reaction, the reaction mixture was then treated in the same manner as in example 1 to give 142 mg of 9-oxo-11α-hydroxymethyl-15β-hydroxy-16,16-dimethylprosta-5(cis),13(-trans)-dienoic acid methylester, 107 mg of a mixture of 9-oxo-11α-hydroxymethyl-15β-hydroxy-16,16-dimethylprosta-5(cis),13(trans)-dienoic acid methylester and 9-oxo-11α-hydroxymethyl-15α-hydroxy-16,16-dimethylprosta-5(cis),13(trans)-dienoic acid methylester and 155 mg of 9-oxo-11α-hydroxymethyl-15α-hydroxy-16,16-dimethylprosta-5(cis),13(trans)-dienoic acid methylester.

IR spectra and NMR spectra of the products agreed with each other.

IR spectra (liquid film) ν $_{max}$cm⁻¹: 3450, 1740.

NMR spectra (CDCl₃) δ: ppm 0.83 (3H, multiplet), 0.87 (6H, singlet), 2.70 (2H, br. singlet), 3.63 (3H, singlet), 5.37 (2H, multiplet), 5.63 (2H, multiplet).

In a mixture solution of 4.8 ml of methanol, 1.2 ml of water and 2.0 ml of a 10% aqueous potassium hydroxide solution was dissolved 150 mg of 9-oxo-11α-hydroxymethyl-15α-hydroxy-16,16-dimethylprosta-

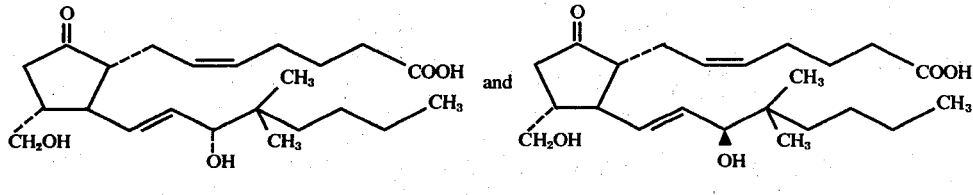

5(cis),13(trans)-dienoic acid methylester, and this solution was stirred at room temperature for 2 hours. After completion of the reaction, the reaction mixture was then treated in the same manner as in example 1 to give 101 mg of 9-oxo-11α-hydroxymethyl-15α- hydroxy-16,16-dimethylprosta-5(cis),13(trans)-dienoic acid as an oil.

In the same manner as above, 130 mg of 9-oxo-11α-hydroxymethyl-15β-hydroxy-16,16-dimethylprosta-5(cis),13(trans)dienoic acid methylester gave 85 mg of 9-oxo-11α-hydroxymethyl15β-hydroxy-16,16-dimethylprosta-5(cis),13(trans)-dienoic acid.

9-Oxo-11α-hydroxymethyl-15α-hydroxy-16,16-dimethylprosta-5(cis),13(trans)-dienoic acid IR spectrum (liquid film) $\nu_{max}$cm$^{-1}$: 3420, 3200 – 2400, 1730, 1710.

NMR spectrum (CD$_3$COCD$_3$) $\beta$: ppm 0.87 (3H, multiplet), 0.89 (6H, singlet), 5.40 (2H, multiplet), 5.67 (2H, multiplet), 6.10 (3H, br. singlet).

9-Oxo-11α-hydroxymethyl-15β-hydroxy-16,16-dimethylprosta-5(cis),13(trans)-dienoic acid IR spectrum (liquid film) $\nu_{max}$cm$^{-1}$: 3400, 3200 –2400, 1730, 1710.

NMR spectrum (CD$_3$COCD$_3$) $\delta$: ppm 0.87 (3H, multiplet), 0.90 (6H, singlet), 5.40 (2H, multiplet), 5.67 (2H, multiplet), 6.20 (3H, br. singlet).

EXAMPLE 6

9-Oxo-11α-hydroxymethyl-15α-hydroxy-16,16-dimethylprosta-5(cis),13(trans)-dienoic acid sodium salt In a mixture solution of 1.0 ml of methanol and 0.1 ml of water was dissolved 42 mg of 9-oxo-11α-hydroxymethyl-15α-hydroxy-16,16-dimethylprosta-5(cis),13(trans)-dienoic acid and to this solution was then added 8.0 mg of sodium carbonate. The resulting mixture was stirred at room temperature 1.5 hours. After completion of the reaction, the reaction mixture was subjected to vacuum evaporation of the solvent to give 46 mg of the desired product as oil.

IR spectrum (liquid film) $\nu_{max}$cm$^{-1}$: 3400, 1730, 1580 ~ 1560.

REFERENCE EXAMPLE 1

2-Benzyloxy-1-iodoethane

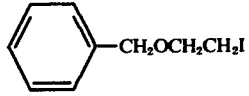

In 69.2 g of pyridine was dissolved 33.27 g of 2-benzyloxy-ethanol, and to this solution was then added with stirring 45.9 g of p-tosyl chloride at an inner temperature in the range of 5°– 10° C. The resulting mixture was stirred at a temperature of 15° C for 2 hours. After completion of the reaction, a mixture solution of 130 ml of conc. hydrochloric acid and 450 ml of ice-water was added to the resulting reaction mixture and then subjected to extraction with benzene. The extract was washed with a saturated aqueous sodium chloride solution and dried over anhydrous sodium sulfate. Upon evaporation of the solvent from the extract, there was obtained 66.9 g of 2-benzyloxy-1-(p-toluenesulfonyloxy)ethane as an oil.

NMR spectrum (CDCl$_3$) $\delta$ : ppm 2.40 (3H, singlet), 3.55 – 3.71 (2H, triplet), 4.10 – 4.27 (2H, triplet), 4.42 (2H, singlet), 7.24 (5H, singlet), 7.20 – 7.30 (2H, doublet), 7.68 – 7.84 (2H, doublet).

In 120 ml of anhydrous hexamethylphosphoroamide (HMPA) were dissolved 66.9 g of 2-benzyloxy-1-(p-toluenesulfonyloxy) ethane obtained by the above reaction and 49.2 g of anhydrous sodium iodide. The resulting solution was then stirred at room temperature for 3 hours followed by stirring at a temperature of 60° C for 1 hour. After completion of the reaction, the reaction mixture was poured into 1.7l of ice-water. To the mixture was added ether, whereby extraction was carried out. The extract was washed with a saturated aqueous sodium chloride solution and dried over anhydrous sodium sulfate. Upon evaporation of the solvent from the extract, there was obtained 54.1 g of an oily substance. The obtained substance was purified by means of column chromatography utilizing 310 g of silica gel. The portions eluted with benzene - hexane (2 : 1) ~ benzene were collected. Upon evaporation of the solvent from the eluate, there was obtained 49.8 g of the desired compound as a pale yellow oil.

NMR spectrum (CDCl$_3$) $\delta$ : ppm 3.12 – 3.39 (2H, triplet), 3.65 – 3.89 (2H, triplet), 4.59 (2H, singlet), 7.33 (5H, singlet).

REFERENCE EXAMPLE 2

2α-(2-Benzyloxyethyl)-2-carboxy-3-hydroxymethyl-4α-ethoxycarbonyloxymethylcyclopentanone-2,3-(γ)-lactone

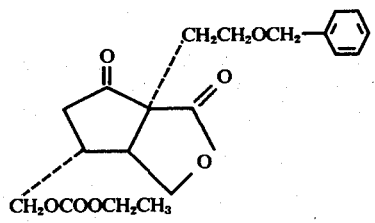

In 200 ml of anhydrous dimethylsulfoxide was dissolved 19.0 g of 2-carboxy-3-hydroxymethyl-4α-ethoxycarbonyloxymethylcyclopentanone-2,3-(γ)-lactone. To this solution was added with stirring and ice-cooling in a stream of argon 14.5 g of 67% potassium t-butoxide followed by stirring 30 minutes at a temperature below 20° C. The reaction mixture turned transparent. To this reaction mixture was subsequently added 28.1 g of 2-benzyloxy-1-iodoethane followed by stirring at room temperature for 4.5 hours. After completion of the reaction, the reaction mixture was poured into a mixture solution of 2l of ice-water and 60 ml of acetic acid. The mixture was then subjected to extraction with ether and with benzene. The extract was washed with a saturated aqueous sodium chloride solution and dried over anhydrous sodium sulfate. Upon evaporation of the solvent from the extract, there was obtained 28 g of an oily substance. The obtained substance was purified by means of column chromatography employing 200 g of silica gel. The portions eluted with benzene - ethyl acetate (90 : 10) were collected. Upon evaporation of the solvent from the eluate, there was obtained 15.54 g of the desired compound as an oil.

IR spectrum (liquid film) $\nu_{max}$cm$^{-1}$: 1794, 1750, 1259, 1027.

NMR spectrum (CDCl$_3$) $\delta$ : ppm 1.17 – 1.43 (3H, triplet), 2.03 – 2.60 (5H, multiplet). 2.86 – 3.27 (1H, multiplet), 3.48 – 3.70 (3H, triplet), 3.91 – 4.56 (5H, multiplet), 4.40 (2H, singlet), 7.33 (5H, singlet).

REFERENCE EXAMPLE 3

2δ-(2-Benzyloxyethyl)-3β-hydroxymethyl-4α-ethoxycarbonyoxymethylcyclopentanone

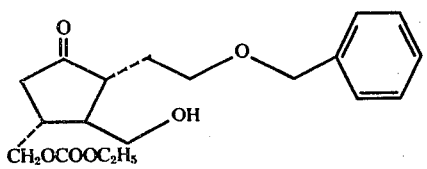

To a mixture solution of 430 ml of pyridine and 430 ml of water was added 19.8 g of 2α-(2-benzyloxyethyl)-2-carboxy-3-hydroxymethyl-4α-ethoxycarbonyloxymethylcyclopentanone-2,3-(γ)-lactone, and the resulting mixture was heated with reflux for 7 hours. After completion of the reaction, the reaction mixture was poured into a mixture solution of ice-water and acetic acid, and saturated with sodium chloride followed by extraction with ethyl acetate. The extract was washed with a saturated aqueous sodium chloride solution, and dried over anhydrous sodium sulfate. Upon evaporation of the solvent from the extract, there was obtained (32.2 g of an oily substance. The obtained substance was purified by means of column chromatography employing 300 g of silica gel. The portions eluted with benzene - ethyl acetate (90 : 10 to 70 : 30) were collected. Upon evaporation of the solvent from the eluate, there was obtained 15.1 g of the desired compound as an oil.

IR spectrum (liquid film) $\nu_{max}$cm$^{-1}$: 3480, 1743, 1258, 1092, 1040.

NMR spectrum (CDCl$_3$) δ : ppm 1.17 – 1.42 (3H, triplet), 1.63 – 2.92 (7H, multiplet), 3.42 – 3.96 (5H, multiplet), 4.02 – 4.50 (4H, multiplet), 7.33 (5H, singelt), 4.50 (2H, singelt).

REFERENCE EXAMPLE 4

2α-(2-Benzyloxyethyl)-3β-(2-tetrahydropyranyloxy)-methyl-4α-ethoxycarbonyloxymethylcyclopentanone

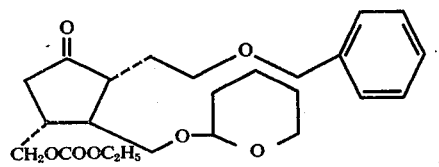

In 150 ml of dichloromethane was dissolved 9.55 g of 2Δ-(2-benzyloxyethyl)-3β-hydroxymethyl-4α-ethoxycarbonyloxymethylcyclopentanone. To the resulting solution were added 3.5 g of dihydropyran and 50 mg of p-toluenesulfonic acid followed by stirring at room temperature for 15 minutes. After completion of the reaction, the reaction mixture was washed with a 2% aqueous sodium hydrogen carbonate solution and with a saturated aqueous sodium chloride solution, and dried over anhydrous sodium sulfate. Upon evaporation of the solvent from the reaction mixture, there was obtained 11.10 g of an oily substance. The obtained substance was purified by means of column chromatography employing 110 g of alumina (Grade II, Woelm Co.). The portions eluted with hexane - benzene (75 : 25 to 60 : 40) were collected. Upon evaporation of the solvent from the eluate, there was obtained 5.05 g of the desired compound as an oil.

IR spectrum (liquid film) $\nu_{max}$cm$^{-1}$: 1748, 1452, 1371, 1255, 1119, 1075, 1022.

NMR spectrum (CDCl$_3$) δ : ppm 1.16 – 1.39 (3H, triplet), 1.43 – 1.69 (6H, multiplet), 1.72 – 2.71 (7H, multiplet), 3.25 – 3.86 (7H, multiplet), 3.91 – 4.35 (3H, multiplet), 4.45 (2H, singlet), 4.43 – 4.66 (1H, multiplet), 7.31 (5H, singlet).

REFERENCE EXAMPLE 5

2α-(2-Benzyloxyethyl)-3β-(2-tetrahydropyranyloxy)-methyl-4α-acetoxymethylcyclopentanone

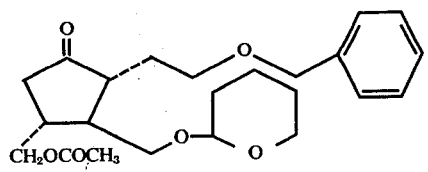

In a mixture solution of 50 ml of methanol, 12.6 ml of water and 10 ml of a 10% aqueous potassium hydroxide solution was dissolved 2.82 g of 2α-(2-benzyloxyethyl)-3β-(2-tetrahydropyranyloxy)methyl-4α-ethoxycarbonyloxymethylcyclopentanone, and the resulting solution was stirred at room temperature for 1 hour. After completion of the reaction, the reaction mixture was poured into a mixture solution of ice-water and acetic acid followed by extraction with ethyl acetate. The extract was washed with a saturated aqueous sodium chloride solution and dried over anhydrous sodium sulfate. Upon evaporation of the solvent from the extract, there was obtained 2.60 g of 2α-(2-benzyloxyethyl)-3β-(2-tetrahydropyranyloxy)methyl-4α-hydroxymethylcyclopentanone as an oil.

In a mixture solution of 16 ml of pyridine and 8 ml of acetic anhydride was dissolved 2.58 g of 2α-(2-benzyloxyethyl)-3β-(2-tetrahydropyranyl)methyl-4β-hydroxymethylcyclopentanone, and the resulting solution was stirred at room temperature for 2 hours. After completion of the reaction, the reaction mixture was poured into a mixture solution of ice-water and acetic acid followed by extraction with benzene. The extract was washed with a saturated aqueous sodium chloride solution and dried over anhydrous sodium sulfate. Upon evaporation of the solvent from the extract, there was obtained 2.84 g of an oily substance. The obtained substance was purified by means of column chromatography utilizing 30 g of silica gel. The portions eluted with benzene ~ benzene - ethyl acetate (90 : 10) were collected. Upon evaporation of the solvent from the eluate, there was obtained 2.30 g of the desired compound as an oil.

IR spectrum (liquid film) $\nu_{max}$cm$^{-1}$: 1740, 1368, 1230, 1018, 1023, 901, 738, 697.

NMR spectrum (CDCl$_3$) δ : ppm 1.24 – 1.74 (6H, multiplet), 2.00 (3H, singlet), 1.74 – 2.75 (7H, multiplet), 3.21 – 4.35 (8H, multiplet), 4.46 (2H, singlet), 4.37 – 4.66 (1H, multiplet), 7.33 (5H, singlet).

REFERENCE EXAMPLE 6

1-Hydroxy-2β-(2-benzyloxyethyl)-3β-(2-tetrahydropyranyloxy)-methyl-4α-acetoxymethylcyclopentane

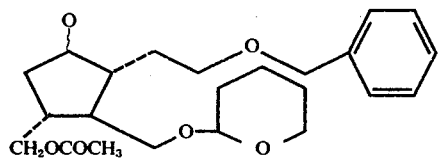

In 40 ml of methanol was dissolved 2.28 g of 2α-(2-benzyloxyethyl)-3β-(2-tetrahydropyranyloxy)methyl-4α-acetoxymethylcyclopentanone, and to this solution was added 426 mg of sodium boron hydride followed by stirring under ice-cooling. After completion of the reaction, the reaction mixture was poured into a mixture solution of ice-water and acetic acid followed by extraction with ethyl acetate. The extract was then dried over anhydrous sodium sulfate. Upon evaporation of the solvent from the extract, there was obtained 2.46 g of the desired compound as an oil.

REFERENCE EXAMPLE 7

1-Acetoxy-2α-(2-benzyloxyethyl)-3β-(2-tetrahydropyranyloxy)-methyl-4α-acetoxymethylcyclopentane

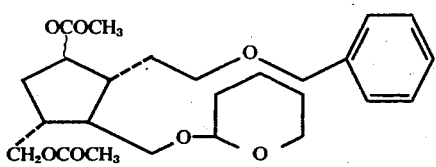

In a mixture solution of 20 ml of pyridine and 5 ml of acetic anhydride was dissolved 2.46 g of 1-hydroxy-2α-(2-benzyloxyethyl)-3β-(2-tetrahydropyranyloxy)methyl-4α-acetoxymethylcyclopentane, and the resulting solution was allowed to stand overnight. After completion of the reaction, the reaction mixture was poured into a mixture solution of ice-water and acetic acid followed by extraction with benzene. The extract was washed with a saturated aqueous sodium chloride solution and dried over anhydrous sodium sulfate. Upon evaporation of the solvent from the extract, there was obtained 3.10 g of an oily substance. The obtained substance was purified by means of column chromatography employing 26 g of silica gel. The portions eluted with hexane - benzene (1 : 1) ~ benzene - acetic acid (95 : 5) were collected. Upon evaporation of the solvent from the eluate, there was obtained 2.28 g of the desired compound as an oil.

IR spectrum (liquid film) $\nu_{max}$cm$^{-1}$: 1741, 1369, 1234, 1118, 1073, 1024, 901, 738, 697.

NMR spectrum (CDCl$_3$) δ : ppm 1.28 – 1.75 (6H, multiplet), 1.99 (3H, singlet), 2.02 (3H, singlet), 1.75 – 2.58 (7H, multiplet), 3.19 – 4.28 (8H, multiplet), 4.46 (2H, singlet). 4.38 – 4.67 (1H, multiplet), 4.88 – 5.34 (1H, multiplet), 7.34 (5H, singlet).

REFERENCE EXAMPLE 8

1-Acetoxy-2α-(2-hydroxyethyl)-3β-(2-tetrahydropyranyloxy)-methyl-4α-acetoxymethylcyclopentane

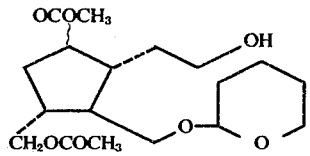

In 70 ml of tetrahydrofuran was dissolved 2.20 g of 1-acetoxy-2α-(2-benzyloxyethyl)-3β-(2-tetrahydropyranyloxy)methyl-4α-acetoxymethylcyclopentane. To this solution was then added 2.20 g of 10% palladium - carbon, an the catalytic reduction was conducted at room temperature under atmospheric pressure for 4 hours. After completion of the reaction, the reaction mixture was filtered to leave insoluble materials. Upon evaporation of the solvent, there was obtained 1.81 g of the desired compound as an oil.

IR spectrum (liquid film) $\nu_{max}$cm$^{-1}$: 3470, 1741, 1440, 1371, 1239, 1120, 1023.

REFERENCE EXAMPLE 9

1-Acetoxy-2α-formylmethyl-3β-(2-tetrahydropyranyloxy)-methyl-4α-acetocymethylcyclopentane

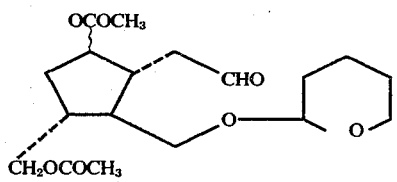

In 90 ml of dichloromethane was dissolved 1.81 g of 1-acetoxy-2α-(2-hydroxyethyl)-3β-(2-tetrahydropyranyloxy)methyl-3α-acetoxymethylcyclopentane, and to this solution was then added 11.6 g of a chromic anhydride - pyridine complex (Collins reagent) followed by stirring at a temperature below 5° C for 30 minutes. After completion of the reaction, ether was added to the reaction mixture followed by filtration by means of Hyflo Super Cel. The filtrate was successively washed under cooling with a 2 % aqueous sodium carbonate solution, a 1 % aqueous hydrochloric acid solution, a 5 % aqueous sodium hydrogen carbonate solution and a saturated aqueous sodium chloride solution, and then dried over anhydrous sodium sulfate. Upon vacuum evaporation of the solvent from the extract at low temperature, there was obtained 1.585 g of the desired compound as an oil.

IR spectrum (liquid film) $\nu_{max}$cm$^{-1}$: 2720, 1732, 1370, 1230, 1120, 1022.

REFERENCE EXAMPLE 10

1-Acetoxy-2α-{6-methoxycarbonyl-2(cis)-hexenyl}-3β-(2-tetrahydropyranyloxy)methyl-4α-acetoxymethylcyclopentane

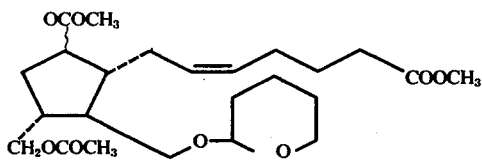

To the solution prepared in a stream of argon from 45 ml of anhydrous dimethyl sulfoxide and 2.25 g of 50 % sodium hydride was added the solution of 10.75 g of 5-triphenylphosphoniopentane acid in 90 ml of anhydrous dimethyl sulfoxide. In 25 ml of anhydrous dimethyl sulfoxide was dissolved 1.580 g of 1-acetoxy-2α-formylmethyl-3β-(2-tetrahydropyranyloxy)methyl-4α-acetoxymethylcyclopentane, and to this solution was added dropwise 60 ml of the above-prepared solution at a temperature below 20° C in a stream of argon followed by stirring for 15 minutes. After completion of the reaction, the reaction mixture was poured into a mixture solution of ice-water and acetic acid followed by extraction with ether. The extract was washed with water and dried over anhydrous sodium sulfate, and stirred after addition of diazomethane. After completion of the reaction, the reaction mixture was washed with water and dried over anhydrous sodium sulfate. Upon evaporation of the solvent from the reaction mixture, there was obtained 3.70 g of an oily substance. The obtained substance was purified by means of column chromatography employing 40 g of silica gel. The portions eluted with benzene - ether (99 : 1 to 95 : 5) were collected. Upon evaporation of the solvent from the eluate, there was obtained 1.110 g of the desired compound as an oil.

IR spectrum (liquid film) $\nu_{max}$cm$^{-1}$: 1740, 1437, 1370, 1238, 1188, 1118, 1027.

NMR spectrum (CDCl$_3$) δ : ppm 2.02, 2.00 (3H×2, singlet), 3.67 (3H, singlet), 2.96 – 4.28 (6H, multiplet), 4.40 – 4.48 (1H, multiplet), 4.69 – 5.27 (1H, multiplet), 5.27 – 5.56 (2H, multiplet).

REFERENCE EXAMPLE 11

1-Acetoxy-2α-{6-methoxycarbonyl-2(cis)-hexenyl}-3β-hydroxymethyl-4α-acetoxymethylcyclopentane

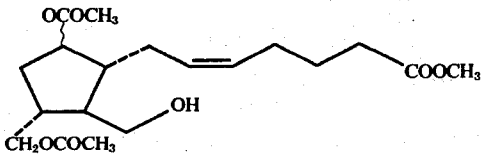

In a mixture solution of 10.4 ml of acetic acid, 10.4 ml of water and 1.5 ml of tetrahydrofuran was dissolved 1.10 g of 1-acetoxy-2α-{6-methoxycarbonyl-2(cis)-hexenyl}-3β-(2-tetrahydropyranyloxy)methyl-4α-acetoxymethylcyclopentane, and the resulting solution was stirred at a temperature of 45° C for 4 hours. After completion of the reaction, to the reaction mixture was added ice-water followed by extraction with ethyl acetate. The extract was washed with a saturated aqueous sodium chloride solution and dried over anhydrous sodium sulfate. Upon evaporation of the solvent from the extract, there was obtained 1.05 g of an oily substance. The obtained substance was purified by means of column chromatography employing 8 g of silica gel. The portions eluted with benzene - ethyl acetate (98 : 2 to 80 : 20) were collected. Upon evaporation of the solvent from the eluate, there was obtained 695 mg of the desired compound as an oil.

IR spectrum (liquid film) $\nu_{max}$cm$^{-1}$: 3400, 1736, 1437, 1370, 1236, 1118, 1027.

NMR spectrum (CDCl$_3$) δ : ppm 2.02 – 2.06 (6H, doublet), 1.33 – 2.69 (14H, multiplet), 3.68 (3H, singlet), 3.52 – 3.79 (2H, multiplet), 3.94 – 4.30 (2H, multiplet), 4.72 – 5.10 (1H, multiplet), 5.10 – 5.60 (2H, multiplet).

REFERENCE EXAMPLE 12

1-Acetoxy-2α-{6-methoxycarbonyl-2(cis)-hexenyl}-3β-formyl-4α-acetoxymethylcyclopentane

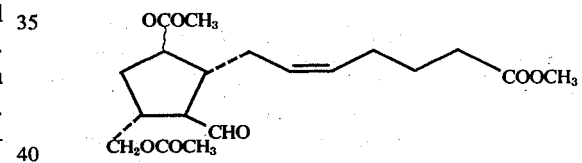

In 20 ml of dichloromethane was dissolved 690 mg of 1-acetoxy-2α-{6-methoxycarbonyl-2(cis)-hexenyl}-3β-hydroxymethyl-4α-acetoxymethylcyclopentane, and to this solution was then added 4.3 g of a chromic anhydride - pyridine complex (Collins reagent) followed by stirring at a temperature below 5° C for 30 minutes. After completion of the reaction, ether was added to the reaction mixture followed by filtration by means of Hyflo Super Cel. The filtrate was successively washed under ice-cooling with a 2 % aqueous sodium carbonate solution, a 1 % aqueous hydrochloric acid solution, a 5 % aqueous sodium hydrogen carbonate solution and a saturated aqueous sodium chloride solution, and dried over anhydrous sodium sulfate. Upon vacuum evaporation of the solvent from the filtrate at low temperature, there was obtained 594 mg of the desired compound as an oil.

NMR spectrum (CDCl$_3$) δ : ppm 2.00 – 2.06 (6H, doublet), 1.56 – 3.00 (13H, multiplet), 3.70 (3H, singlet), 3.90 – 4.31 (2H, multiplet), 4.94 – 5.24 (1H, multiplet), 5.24 – 5.60 (2H, multiplet), 9.70 – 9.96 (1H, multiplet).

REFERENCE EXAMPLE 13

9-Acetoxy-11α-acetoxymethyl-15-oxoprosta-5(cis),13(trans)-dienoic acid methylester

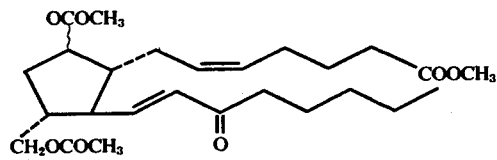

In 30 ml of anhydrous ether was dissolved 590 mg of 1-acetoxy-2α-{6-methoxycarbonyl-2(cis)-hexenyl}-3β-formyl4α-acetoxymethylcyclopentane, and to this solution was then added 694 mg of 2-oxoheptylidene-tri-n-butylphosphorane followed by stirring overnight at room temperature in a stream of argon. After completion of the reaction, the solvent was evaporated under reduced pressure from the reaction mixture to give 1.29 g of an oily substance. The obtained substance was purified by means of column chromatography employing 10.5 g of silica gel. The portions eluted with benzene ∼ benzene - ether (98 : 2) were collected. Upon evaporation of the solvent from the eluate, there was obtained 565 mg of the desired compound as an oil.

IR spectrum (liquid film) $\nu_{max}cm^{-1}$: 1741, 1701, 1677, 1630, 1439, 1370, 1238, 1191, 1119, 1030.

NMR spectrum (CDCl$_3$) δ : ppm 0.73 – 1.10 (3H, triplet), 2.00 – 2.06 (6H, triplet), 1.10 – 2.95 (21H, multiplet), 3.68 (3H, singlet), 3.90 – 4.23 (2H, multiplet), 4.79 – 5.27 (1H, multiplet), 5.27 – 5.66 (2H, multiplet), 5.96 – 6.40 (1H, quartet), 6.49 – 7.00 (1H, multiplet).

REFERENCE EXAMPLE 14

9-Acetoxy-11α-acetoxymethyl-15-hydroxyprosta-5(cis),13-(trans)-dienoic acid methylester

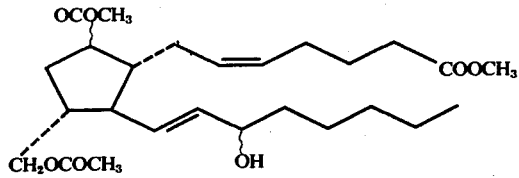

In 23 ml of methanol was dissolved 561 mg of 9-acetoxy-11α-acetoxymethyl-15-oxoprosta-5(cis),13(-trans)-dienoic acid methylester, and to this solution was then added 93 mg of sodium boron hydride followed by stirring at a temperature below 5° C for 20 minutes. After completion of the reaction, the reaction mixture was poured into a mixture solution of ice-water and acetic acid followed by extraction with ethyl acetate. The extract was dried over anhydrous sodium sulfate. Upon evaporation of the solvent from the extract, there was obtained 572 mg of the desired compound as an oil.

REFERENCE EXAMPLE 15

9-Acetoxy-11α-acetoxymethyl-15-(2-tetrahydropyranyl)oxyprosta-5(cis),13(trans)-dienoic acid methylester

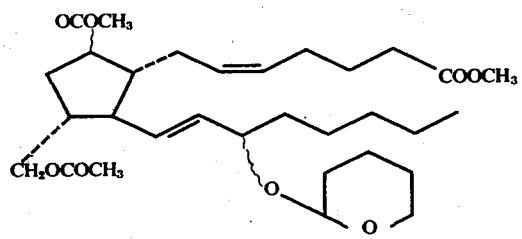

In 8 ml of dichloromethane was dissolved 572 mg of 9-acetoxy-11α-acetoxymethyl-15-hydroxyprosta-5(cis),13(trans)dienoic acid methylester, and to this solution were then added 600 mg of dihydropyran and 10 mg of p-toluenesulfonic acid followed by stirring at room temperature for 20 minutes. After completion of the reaction, the reaction mixture was washed with a 2 % aqueous sodium hydrogen carbonate solution and with a saturated aqueous sodium chloride solution, and dried over anhydrous sodium sulfate. Upon evaporation of the solvent from the reaction mixture, there was obtained 700 mg of an oily substance. The obtained substance was purified by means of column chromatography employing 7 g of silica gel. The portions eluted with benzene - ether (99 : 1 to 95 : 5) were collected. Upon evaporation of the solvent from the eluate, there was obtained 496 mg of the desired compound as an oil.

IR spectrum (liquid film) $\nu_{max}cm^{-1}$: 1740, 1437, 1370, 1234, 1112, 1017, 972.

NMR spectrum (CDCl$_3$) δ : ppm 0.73 – 1.10 (3H, triplet), 2.04 (6H, singlet), 1.10 – 2.64 (21H, multiplet), 3.68 (3H, singlet), 3.26 – 4.26 (4H, multiplet), 4.53 – 5.20 (3H, multiplet), 5.20 – 5.67 (4H, multiplet).

REFERENCE EXAMPLE 16

9-Hydroxy-11α-trichloroacetyloxymethyl-15-(2-tetrahydropyranyl)oxyprosta-5(cis),13(trans)-dienoic acid methylester

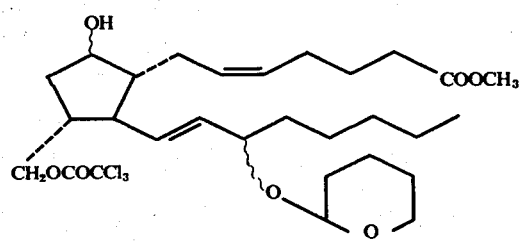

In 7.2 ml of anhydrous methanol was dissolved 491 mg of 9-acetoxy-11α-acetoxymethyl-15-(2-tetrahydropyranyl)oxyprosta-5(cis),13(trans)-dienoic acid methylester, and to this solution was then added 180 mg of anhydrous potassium carbonate followed by stirring at room temperature for 6 hours. After completion of the reaction, the reaction mixture was poured into a mixture solution of ice-water and acetic acid followed by extraction with ether. The extract was washed with a saturated aqueous sodium chloride solution, and dried over anhydrous sodium sulfate. Upon evaporation of the solvent from the extract, there was obtained 396 mg of 9-hydroxy-11α-hydroxymethyl-15-(2-tetrahydropyranyl)oxyprosta-5(cis),13(trans)-dienoic acid methylester as an oil.

IR spectrum (liquid film) $\nu_{max}cm^{-1}$: 3400, 1743, 1438, 1195, 1111, 1072, 1018, 981.

NMR spectrum (CDCl$_3$) δ : ppm 0.68 – 1.09 (3H, triplet), 1.09 – 2.62 (27H, multiplet), 2.50 (2H, singlet), 3.67 (3H, singlet), 3.20 – 4.31 (6H, multiplet), 4.50 – 4.82 (1H, multiplet), 5.00 – 5.78 (4H, multiplet).

In 6 ml of anhydrous toluene was dissolved 392 mg of 9-hydroxy-11α-hydroxymethyl-15-(2-tetrahydropyranyl)oxyprosta-5(cis),13(trans)-dienoic acid methylester, and to this solution were then added in a stream of argon 930 mg of triethylamine and 164 mg of trichloroacetyl chloride followed by stirring at a temperature of −70° C for 30 minutes. After completion of the reaction, the reaction mixture was poured into a mixture solution of ice-water and acetic acid followed by extraction with ether. The extract was washed with a saturated aqueous sodium chloride solution, and dried over anhydrous sodium sulfate. Upon evaporation of the solvent from the extract, there was obtained 545 mg of an oily substance. The obtained substance was purified by means of column chromatography employing 5.4 g of silica gel. The portions eluted with benzene —ether (98 : 2 to 90 : 10) were collected. Upon evaporation of the solvent from the eluate, there was obtained 368 mg of the desired compound as an oil.

IR spectrum (liquid film) $\nu_{max}cm^{-1}$: 3450, 1770, 1743, 1439, 1240, 1018, 980, 825.

NMR spectrum (CDCl$_3$) δ : ppm 0.70 – 1.04 (3H, triplet), 1.04 – 2.67 (27H, multiplet), 3.63 (3H, singlet), 3.20 – 4.48 (7H, multiplet), 4.53 – 4.74 (1H, multiplet), 5.20 – 5.65 (4H, multiplet).

REFERENCE EXAMPLE 17

9-Hydroxy-11α-trichloroacetyloxymethyl-15-(2-tetrahydropyranyl)oxyprosta-5(cis),13(trans)-dienoic acid

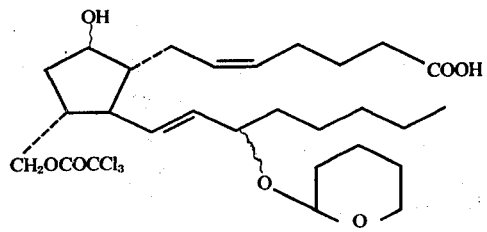

In a solution of 50 ml of methanol, 12.5 ml of water and 20 ml of 10% potassium hydroxide was dissolved 511 mg of 9-acetoxy-11α-acetoxymethyl-15-(2-tetrahydropyranyl)oxyprosta-5(cis),13(trans)-dienoic acid methylester, and the resulting solution was stirred at room temperature for 3 hours. After completion of the reaction, the reaction mixture was poured into a mixture solution of ice-water and acetic acid followed by extraction with ether. The extract was washed with a saturated aqueous sodium chloride solution, and dried over anhydrous sodium sulfate. Upon evaporation of the solvent from the extract, there was obtained 490 mg of an oily substance. The obtained substance was purified by means of column chromatography employing 5 g of silica gel. The portions eluted with benzene —ethyl acetate (90 : 10 to 80 : 20) were collected. Upon evaporation of the solvent from the eluate, there was obtained 425 mg of 9hydroxy-11α-hydroxymethyl-15-(2-tetrahydropyranyl)oxyprosta-5(cis),13(trans)-dienoic acid as an oil.

IR spectrum (liquid film) $\nu_{max}cm^{-1}$: 3390, 1708.

NMR spectrum (CDCl$_3$) δ : ppm 5.20 – 5.69 (4H, multiplet).

In 10 ml of anhydrous toluene was dissolved 420 mg of 9-hydroxy-11α-hydroxymethyl-15-(2-tetrahydropyranyl)oxyprosta-5(cis),13(trans)-dienoic acid, and to this solution were then added in a stream of argon 1.5 g of triethylamine and 186 mg of trichloroacetyl chloride followed by stirring at a temperature of −70° C for 30 minutes. After completion of the reaction, the reaction mixture was poured into a mixture solution of ice-water and acetic acid followed by extraction with ether. The extract was washed with a saturated aqueous sodium chloride solution, and dried over anhydrous sodium sulfate. Upon evaporation of the solvent from the extract, there was obtained 572 mg of an oily substance. The obtained substance was purified by means of column chromatography employing 5.7 g of silica gel. The portions eluted with benzene —ethyl acetate (95 : 5 to 90 : 10) were collected. Upon evaporation of the solvent from the eluate, there was obtained 402 mg of the desired compound as an oil.

IR spectrum (liquid film) $\nu_{max}$cm$^{-1}$: 3430, 1770, 1711.

NMR spectrum (CDCl$_3$) δ : ppm 5.21 – 5.71 (4H, multiplet).

REFERENCE EXAMPLE 18

9-Acetoxy-11α-acetoxymethyl-15-oxo-20-ethylprosta-5(cis),13(trans)-dienoic acid methylester

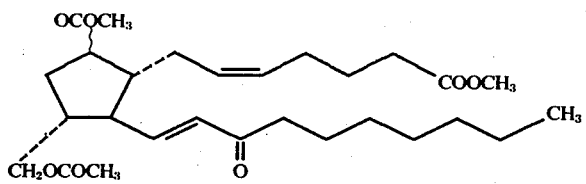

In 50 ml of anhydrous ether was dissolved 2.50 g of 1-acetoxy-2α-(6-methoxycarbonyl-2(cis)-hexenyl)-3β-formyl-4α-acetoxymethylcyclopentane. To this solution was added 2.9 g of 2-oxononylidene-tri-n-butylphosphorane was added, and the mixture was stirred at room temperature in a stream of argon for 18 hours. After completion of the reaction, the reaction mixture was then treated in the same manner as in reference example 13 to give 2.75 g of the desired compound as an oil.

IR spectrum (liquid film) $\nu_{max}$cm$^{-1}$: 1742, 1698, 1675, 1630.

NMR spectrum (CDCl$_3$) δ : ppm 0.9 (3H, multiplet), 2.00 – 2.05 (6H, triplet), 3.67 (3H, singlet), 4.8 – 5.2 (1H, multiplet), 5.3 – 5.6 (2H, multiplet), 6.05 (1H, doublet), 6.64 (1H, multiplet).

REFERENCE EXAMPLE 19

9-Acetoxy-11α-acetoxymethyl-15-hydroxy-20-ethylprosta-5(cis),13(trans)-dienoic acid methylester

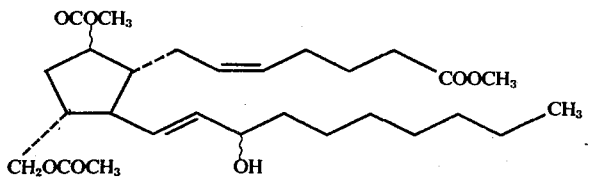

In 40 ml of anhydrous methanol was dissolved 1.30 g of 9-acetoxy-11α-acetoxymethyl-15-oxo-20-ethylprosta-5(cis),13(trans)-dienoic acid methylester. To this solution was added 190 mg of sodium boron hydride, and the mixture was stirred at a temperature below 5° C for 20 minutes. After completion of the reaction, the reaction mixture was then treated in the same manner as in reference example 14 to give 1.31 g of the desired compound as an oil.

REFERENCE EXAMPLE 20

9-Acetoxy-11α-acetoxymethyl-15-(2-tetrahydropyranyl)oxy-20-ethylprosta-5(cis),13(trans)-dienoic acid methylester

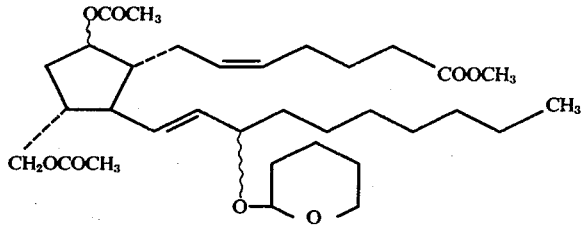

In 20 ml of anhydrous dichloromethane was dissolved 1.31 g of 9-acetoxy-11α-acetoxymethyl-15-hydroxy-20-ethylprosta-5(cis),13(trans)-dienoic acid methylester. To this solution were added 1.2 g of dihydropyran and 20 mg of p-toluenesulfonic acid, and the mixture was stirred at room temperature for 20 minutes. After completion of the reaction, the reaction mixture was then treated in the same manner as in reference example 15 to give 958 mg of the desired compound as an oil.

IR spectrum (liquid film) $\nu_{max}$cm$^{-1}$: 1740, 1114, 1018.

NMR spectrum (CDCl$_3$) δ : ppm 0.86 (3H, multiplet), 2.02 (6H, singlet), 3.68 (3H, singlet), 4.5 – 5.2 (3H, multiplet), 5.2 – 5.7 (4H, multiplet).

REFERENCE EXAMPLE 21

9-Hydroxy-11α-trichloroacetyloxymethyl-15-(2-tetrahydropyranyl)oxy-20-ethylprosta-5(cis),13(trans)-dienoic acid methylester

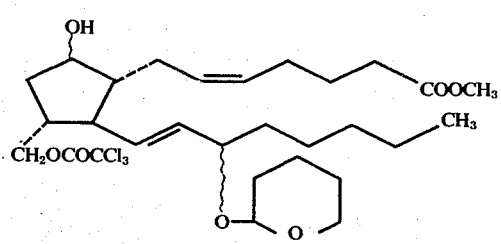

In 14 ml of anhydrous methanol was dissolved 950 mg of 9-acetoxy-11α-acetoxymethyl-15-(2-tetrahydropyranyl)oxy-20-ethylprosta-5(cis),13(trans)-dienoic acid methylester. To this solution was added 170 mg of anhydrous potassium carbonate, and the mixture was stirred at room temperature for 6 hours. After completion of the reaction, the reaction mixture was then treated in the same manner as in reference example 16 to give 788 mg of 9-hydroxy-11α-hydroxymethyl-15-(2-tetrahydropyranyl)oxy-20-ethylprosta-5(cis),13(trans)-dienoic acid methylester as an oil.

IR spectrum (liquid film) $\nu_{max}cm^{-1}$: 3400, 1742, 1110, 1018.

In 15 ml of anhydrous toluene was dissolved 788 mg of 9-hydroxy-11α-hydroxymethyl-15-(2-tetrahydroxypyranyl)oxy-20-ethylprosta-5(cis),13(trans)-dienoic acid methylester. To this solution were added 1.8 g of triethylamine and 318 mg of trichloroacetyl chloride in a stream of argon, and the mixture was stirred at a temperature of −70° C for 30 minutes. After completion of the reaction, the reaction mixture was then treated in the same manner as in reference example 16 to give 745 mg of the desired compound as an oil.

IR spectrum (liquid film) $\nu_{max}cm^{-1}$: 3450, 1770, 1742, 1018.

NMR spectrum (CDCl$_3$) δ : ppm 0.86 (3H, multiplet), 3.65 (3H, singlet), 4.55 – 4.75 (1H, multiplet), 5.20 – 5.66 (4H, multiplet).

REFERENCE EXAMPLE 22

9-Acetoxy-11α-acetoxymethyl-15-oxo-16,16-dimethylprosta-5(cis),13(trans)-dienoic acid methylester

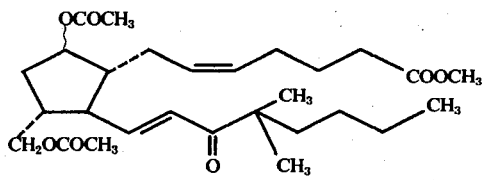

In 30 ml of anhydrous dioxane was dissolved 1.40 g of 1-acetoxy-2α-(6-methoxycarbonyl-2(cis)-hexenyl)3β-formyl-4α-acetoxymethylcyclopentane. To this solution was added 1.56 g of 2-oxo-3,3-dimethylheptylidene-tri-n-butylphosphorane, and the mixture was heated with reflux for 3 days in a stream of argon. After completion of the reaction, the reaction mixture was then treated in the same manner as in reference example 13 to give 1.53 g of the desired compound as an oil.

IR spectrum (liquid film) $\nu_{max}cm^{-1}$: 1743, 1695, 1620.

NMR spectrum (CDCl$_3$) δ : ppm 0.88 (3H, multiplet), 1.10 (6H, singlet), 2.00 – 2.06 (6H, triplet), 3.68 (3H, singlet), 4.8 – 5.2 (1H, multiplet), 5.3 – 5.6 (2H, multiplet), 6.30 (1H, doublet), 6.80 (1H, multiplet).

REFERENCE EXAMPLE 23

9-Acetoxy-11α-acetoxymethyl-15-hydroxy-16,16-dimethylprosta-5(cis),13(trans)-dienoic acid methylester

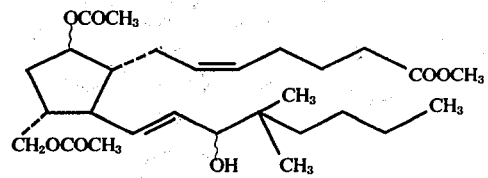

In 50 ml of anhydrous methanol was dissolved 150 g of 9-acetoxy-11α-acetoxymethyl-15-oxo-16,16-dimethylprosta-5(cis),13(trans)-dienoic acid methylester. To this solution was added 220 mg of sodium boron hydride, and the mixture was stirred at a temperature below 5° C for 20 minutes. After completion of the reaction, the reaction mixture was then treated in the same manner as in reference example 14 to give 1.51 g of the desired compound as an oil.

REFERENCE EXAMPLE 24

9-Acetoxy-11α-acetoxymethyl-15-(2-tetrahydropyranyl)oxy-16,16-dimethylprosta-5(cis),13(trans)-dienoic acid methylester

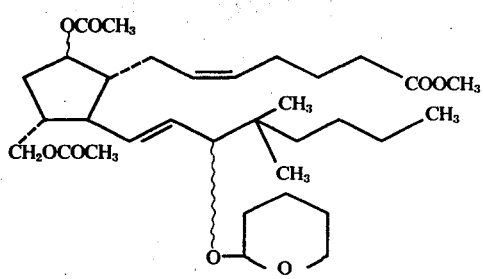

In 30 ml of anhydrous dichloromethane was dissolved 1.51 g of 9-acetoxy-11α-acetoxymethyl-15-hydroxy-16,16-dimethylprosta-5(cis),13(trans)-dienoic acid methylester. To this solution were added 1.4 g of dihydropyran and 25 mg of p-toluenesulfonic acid, and the mixture was stirred at room temperature for 20 minutes. After completion of the reaction, the reaction mixture was then treated in the same manner as in reference example 15 to give 1.12 g of the desired compound as an oil.

IR spectrum (liquid film) $\nu_{max}cm^{-1}$: 1742, 1112, 1018.

NMR spectrum (CDCl$_3$) δ : ppm 0.80, 0.87 and 0.9 (9H, singlet and multiplet), 2.01 (6H, singlet), 3.68 (3H, singlet), 4.5 – 5.15 (3H, multiplet), 5.15 – 5.65 (4H, multiplet).

REFERENCE EXAMPLE 25

9-Hydroxy-11α-trichloroacetyloxymethyl-15-(2-tetrahydropyranyl)oxy-16,16-dimethylprosta-5(cis),13(trans)-dienoic acid methylester

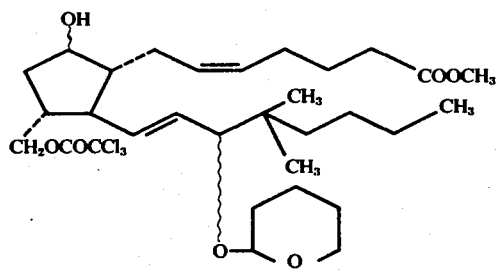

In 16 ml of anhydrous methanol was dissolved 1.10 g of 9-acetoxy-11α-acetoxymethyl-15-(2-tetrahydropyranyl)oxy-16,16-dimethylprosta-5(cis),13(trans)-dienoic acid methylester. To this solution was added 195 mg of anhydrous potassium carbonate, and the mixture was stirred at room temperature for 6 hours. After completion of the reaction, the reaction mixture was then treated in the same manner as in reference example 16 to give 900 mg of 9-hydroxy-11α-hydroxymethyl-15-(2-tetrahydropyranyl)oxy-16,16-dimethylprosta-5(cis),13(trans)-dienoic acid as an oil.

IR spectrum (liquid film) $\nu_{max}$cm$^{-1}$: 3400, 1740, 1110, 1017.

In 20 ml of anhydrous toluene was dissolved 900 mg of 9-hydroxy-11α-hydroxymethyl-15-(2-tetrahydropyranyl)oxy-16,16-dimethylprosta-5(cis),13(trans)-dienoic acid methylester. To this solution were added 2.05 g of triethylamine and 362 mg of trichloroacetyl chloride in a stream of argon, and the mixture was stirred at a temperature of −70° C for 30 minutes. After completion of the reaction, the reaction mixture was then treated in the same manner as in reference example 16 to give 855 mg of the desired compound as an oil.

IR spectrum (liquid film) $\nu_{max}$cm$^{-1}$: 3450, 1770, 1740, 1018.

NMR spectrum (CDCl$_3$) δ : ppm 0.80, 0.90 and 0.95 (9H, singlet and multiplet), 3.68 (3H, singlet), 4.60 (1H, multiplet), 5.2 – 5.6 (4H, multiplet).

What we claim is:
1. Compounds having the formula

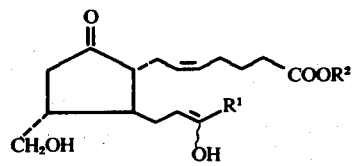

wherein R$^1$ is 1,1-dimethylpentyl and R$^2$ represents hydrogen atom or a straight or branched alkyl group having from one to 6 carbon atoms, and pharmaceutically acceptable salts thereof.

2. 9-Oxo-11α-hydroxymethyl-15α (or β)-hydroxy-16,16-dimethylprosta-5(cis),13(trans)-dienoic acid and pharmaceutically acceptable salts thereof.

3. Methyl 9-oxo-11α-hydroxymethyl-15α (or β)-hydroxy-16,16-dimethylprosta-5(cis),13(trans)-dienoate.

4. Potassium 9-oxo-11α-hydroxymethyl-15α (or β)-hydroxy-16,16-dimethylprosta-5(cis),13(trans)-dienoate.

* * * * *

UNITED STATES PATENT OFFICE
CERTIFICATE OF CORRECTION

Patent No. 4,012,429       Dated March 15, 1977

Inventor(s)  Kiyoshi Sakai et al.

It is certified that error appears in the above-identified patent and that said Letters Patent are hereby corrected as shown below:

Column 3, Table 1, in the second Test compound: "16,26" should read -- 16,16 --.

Column 20, line 48: "15" should read -- 15α --.

Column 21, line 23: ".06-2.88" should read -- 1.06-2.88 --.

Column 22, line 6, "-15βB-" should read -- -15β- --.

Column 22, line 19, "15α-" should read -- 15β- --.

Column 29, line 26: delete "(".

Column 29, line 54; "2Δ" should read -- 2α --.

Column 31, line 3: "2 " should read -- 2α --.

*Signed and Sealed this*

*Sixth* Day of *September 1977*

[SEAL]

Attest:

RUTH C. MASON  
*Attesting Officer*

LUTRELLE F. PARKER  
*Acting Commissioner of Patents and Trademarks*

UNITED STATES PATENT AND TRADEMARK OFFICE
CERTIFICATE OF CORRECTION

PATENT NO. : 4,012,429
DATED : March 15, 1977
INVENTOR(S) : KIYOSHI SAKAI et al

It is certified that error appears in the above-identified patent and that said Letters Patent are hereby corrected as shown below:

Delete the title and replace it with the following title:

---16,16-DIMETHYL 9-OXO-11α-HYDROXYMETHYL-15ξ-HYDROXYPROSTA-5(CIS),13(TRANS)-DIENOIC ACID DERIVATIVES AND PROCESS FOR THE PREPARATION THEREOF---.

Signed and Sealed this

*Twenty-seventh* Day of *November 1979*

[SEAL]

*Attest:*

RUTH C. MASON
*Attesting Officer*

LUTRELLE F. PARKER
*Acting Commissioner of Patents and Trademarks*